US 12,280,099 B2

(12) United States Patent
Kohara et al.

(10) Patent No.: US 12,280,099 B2
(45) Date of Patent: Apr. 22, 2025

(54) DENGUE VIRUS VACCINE

(71) Applicants: TOKYO METROPOLITAN INSTITUTE OF MEDICAL SCIENCE, Tokyo (JP); KAGOSHIMA UNIVERSITY, Kagoshima (JP); NAGASAKI UNIVERSITY, Nagasaki (JP)

(72) Inventors: Michinori Kohara, Tokyo (JP); Fumihiko Yasui, Tokyo (JP); Daisuke Yamane, Tokyo (JP); Kyoko Kohara, Kagoshima (JP); Kouichi Morita, Nagasaki (JP); Yasuhiro Yasutomi, Ibaraki (JP); Koji Ishii, Tokyo (JP)

(73) Assignees: TOKYO METROPOLITAN INSTITUTE OF MEDICAL SCIENCE, Tokyo (JP); KAGOSHIMA UNIVERSITY, Kagoshima (JP); NAGASAKI UNIVERSITY, Nagasaki (JP)

( * ) Notice: Subject to any disclaimer, the term of this patent is extended or adjusted under 35 U.S.C. 154(b) by 848 days.

(21) Appl. No.: 17/438,178

(22) PCT Filed: Mar. 13, 2020

(86) PCT No.: PCT/JP2020/012569
§ 371 (c)(1),
(2) Date: Oct. 1, 2021

(87) PCT Pub. No.: WO2020/184730
PCT Pub. Date: Sep. 17, 2020

(65) Prior Publication Data
US 2022/0152187 A1     May 19, 2022

(30) Foreign Application Priority Data

Mar. 14, 2019   (JP) .................................. 2019-047582

(51) Int. Cl.
*A61K 39/12* (2006.01)
*A61P 31/14* (2006.01)
*C12N 15/113* (2010.01)
*A61K 39/00* (2006.01)

(52) U.S. Cl.
CPC .............. *A61K 39/12* (2013.01); *A61P 31/14* (2018.01); *C12N 15/1131* (2013.01); *A61K 2039/5254* (2013.01)

(58) Field of Classification Search
None
See application file for complete search history.

(56) References Cited

U.S. PATENT DOCUMENTS 11,111,481 B2 *  9/2021  Tuller .................... A61K 39/12
2006/0029619 A1  2/2006  Howley et al.
2006/0159699 A1  7/2006  Howley et al.
2010/0047280 A1  2/2010  Howley et al.
2010/0136054 A1  6/2010  Howley et al.

FOREIGN PATENT DOCUMENTS

| JP | 3-503364 A | 8/1991 |
| JP | 2005-511042 A | 4/2005 |
| JP | 2005-525821 A | 9/2005 |
| JP | 2013-48597 A | 3/2013 |
| WO | WO 90/01946 A1 | 3/1990 |
| WO | WO 2006/013815 A1 | 2/2006 |

OTHER PUBLICATIONS

Parrish et al. (Archives in Virology, 1991, p. 279-286).*
Ishii et al. (Viology 2002, p. 433-444).*
Indonesian Office Action for Indonesian Application No. P00202108571, dated May 25, 2023, with an English translation.
Japanese Notice of Reasons for Refusal for Japanese Application No. 2020-044530, dated Jan. 23, 2024, with an English translation.
Falgout et al., "Immunization of Mice with Recombinant Vaccinia Virus Expressing Authentic Dengue Virus Nonstructural Protein NS1 Protects against Lethal Dengue Virus Encephalitis," Journal of Virology (1990), vol. 64, No. 9, pp. 4356-4363.
International Search Report mailed Jun. 23, 2020, in PCT/JP2020/012569.
The World Health Organization (WHO), "Who advises Dengvaxia be used only in people previously infected with dengue" 2017 (https:/www.who.int/medicines/news/2017/WHO-advises-dengvaxia-used-only-in-people-previously-infected/en/).
Dengue vaccine: WHO position paper, Weekly epidemiological record (Jul. 2016), vol. 91, No. 30, pp. 349-364.
Extended European Search Report for European Application No. 20770940.3, dated Jan. 2, 2023.
Ishii et al., "Structural Analysis of Vaccinia Virus Dls Strain: Application as a New Replication-Deficient Viral Vector," Virology, vol. 302, 2002, pp. 433-444.
Kapoor et al., "Association between NS3 and NS5 Proteins of Dengue Virus Type 2 in the Putative RNA Replicase Is Linked to Differential Phosphorylation of NS5*," The Journal of Biological Chemistry, vol. 270, No. 32, 1995, pp. 19100-19106.

(Continued)

*Primary Examiner* — Agnieszka Boesen
(74) *Attorney, Agent, or Firm* — Birch, Stewart, Kolasch & Birch, LLP

(57) ABSTRACT

The present invention provides a recombinant Vaccinia virus as a dengue virus vaccine that can be used as a therapeutic or prophylactic agent in the clinic. This recombinant Vaccinia virus is characterized by including: all or part of a cDNA that encodes a non-structural protein from a dengue virus; and an expression promoter.

Figure 1:
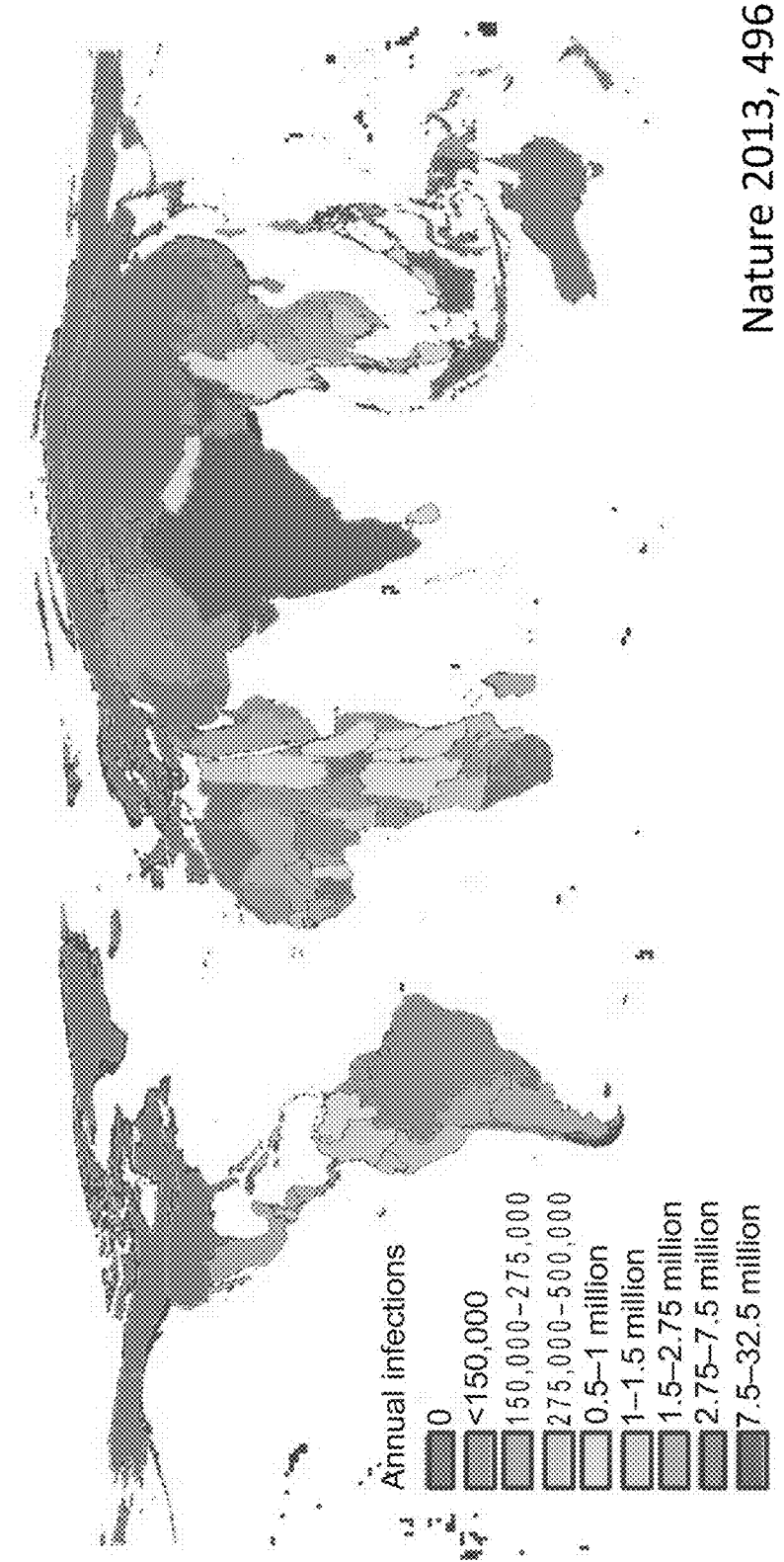

11 Claims, 17 Drawing Sheets
(15 of 17 Drawing Sheet(s) Filed in Color)
Specification includes a Sequence Listing.

(56) References Cited

OTHER PUBLICATIONS

Phadungsombat et al., "Emergence of genotype Cosmopolitan of dengue virus type 2 and genotype III of dengue virus type 3 in Thailand," PLOS One, vol. 13, No. 11, 2018, pp. 1-26.
Tripathi et al., "Recent Developments in Recombinant Protein-Based Dengue Vaccines," Frontiers in Immunology, vol. 9, 2018, pp. 1-15.

* cited by examiner

Fig. 2

| Name | Developer | Features | Current status |
|---|---|---|---|
| CYD | Sanofi | Quadrivalent vaccine using chimeric virus having yellow fever vaccine virus backbone | Approved in Mexico in 2015 |
| DENVax | Takeda | Quadrivalent vaccine using chimeric virus having attenuated dengue type 2 virus backbone | Undergoing Phase 3 |
| TV003/TV005 | Butantan, etc. | Quadrivalent vaccine using attenuated virus deficient in 3' untranslated region and chimeric virus using the same as backbone | Undergoing Phase 2 |
| TDEN | WRAIR, etc. | Quadrivalent live vaccine attenuated by passage | Undergoing Phase 2 |
| PIV | WRAIR, etc. | Alum-adjuvanted vaccine inactivated by purified formalin (currently evaluated for type 1 only) | Undergoing Phase 1 |

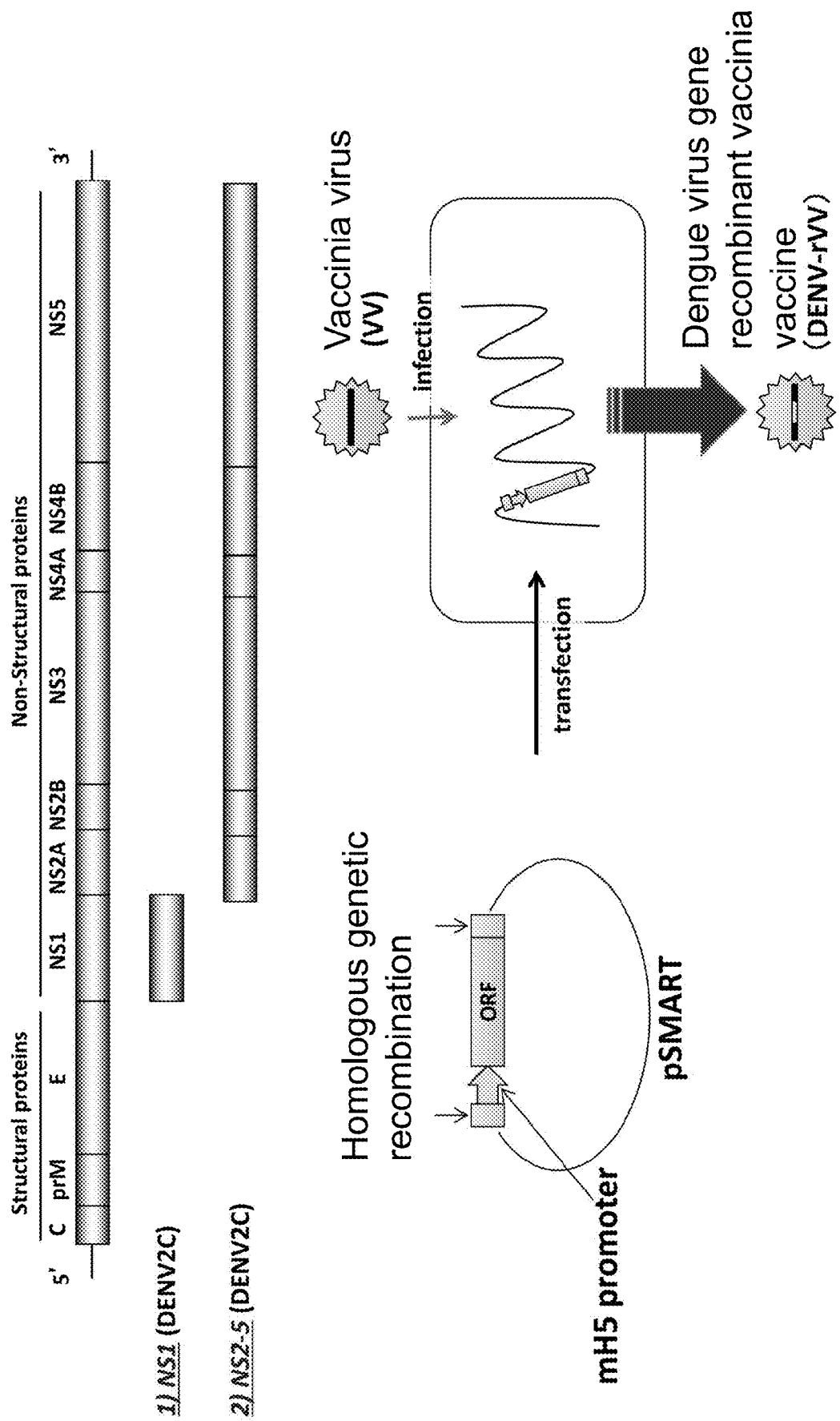

Fig. 4

1. Induction of cellular immunity-type recombinant vaccine

Effective in preventing antibody-dependent enhancement (ADE)

2. Induction of cellular immunity-type recombinant vaccine

Effective in preventing antibody-dependent enhancement (ADE)

Parent vaccine
Dis strain

Fig. 5
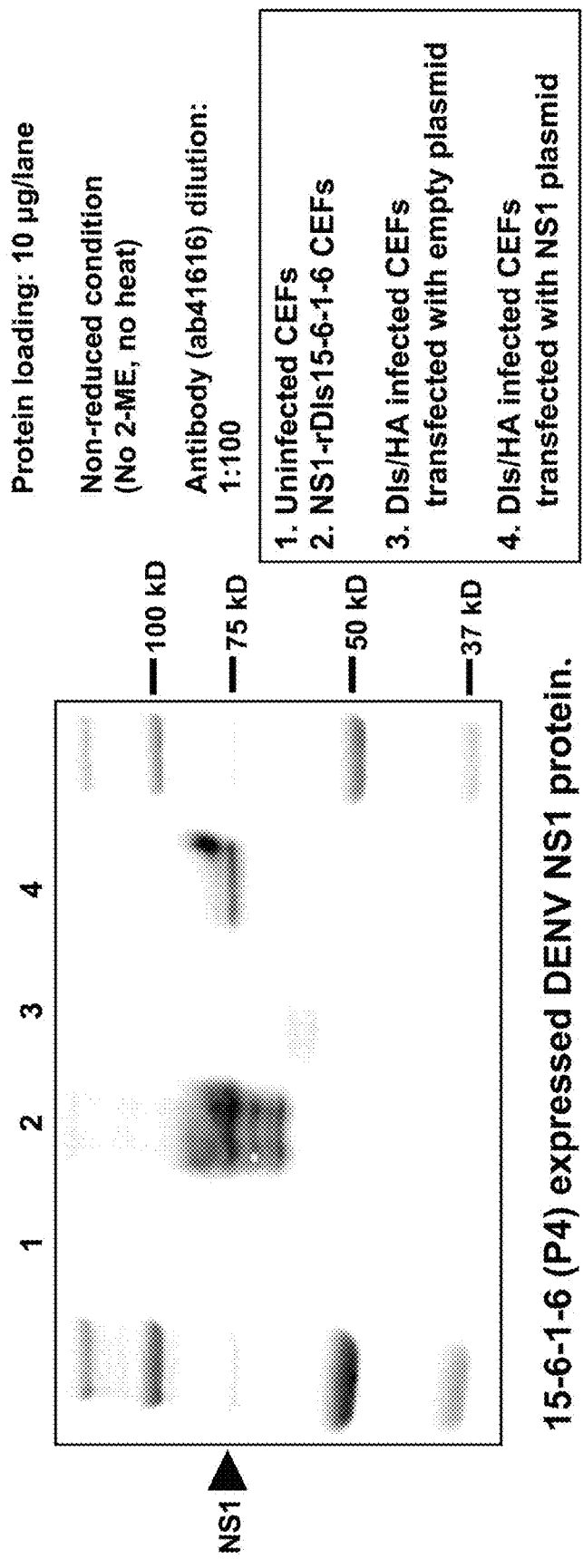
15-6-1-6 (P4) expressed DENV NS1 protein.
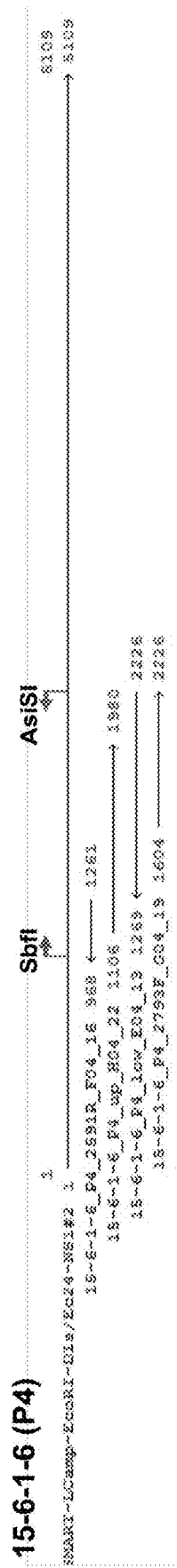
DNA sequences (SbfI→ mH5 promoter→ Ec24-NS1→ 3X stop codon→ AsiSI) were correct in 15-6-1-6 clone.

1. rDIs-DENV2C-NS25
P4 Expansion (Nissui&GIBCO GlutaMAX medium)

| | pfu/mL |
|---|---|
| P4-Nissui (Ha:180422So:180510) 544mL | 2.2E7 |
| P4-GIBCO (Ha:180422So:180510) 561mL | 4.8E7 |

Concentration (30 fold)

Conc

| | pfu/mL |
|---|---|
| P4-Nissui (Ha:180422So:180510) 18mL | 4.2E8 |
|

Fig. 9
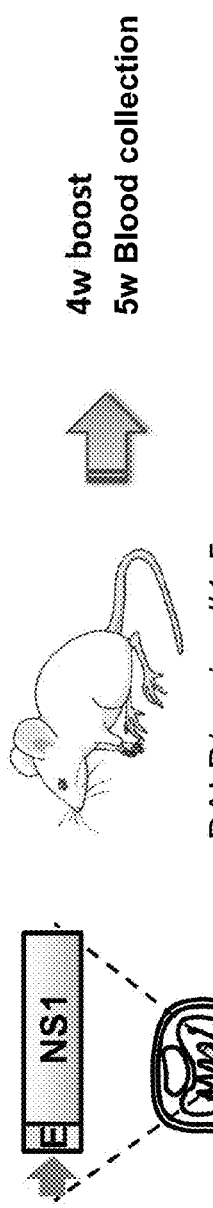
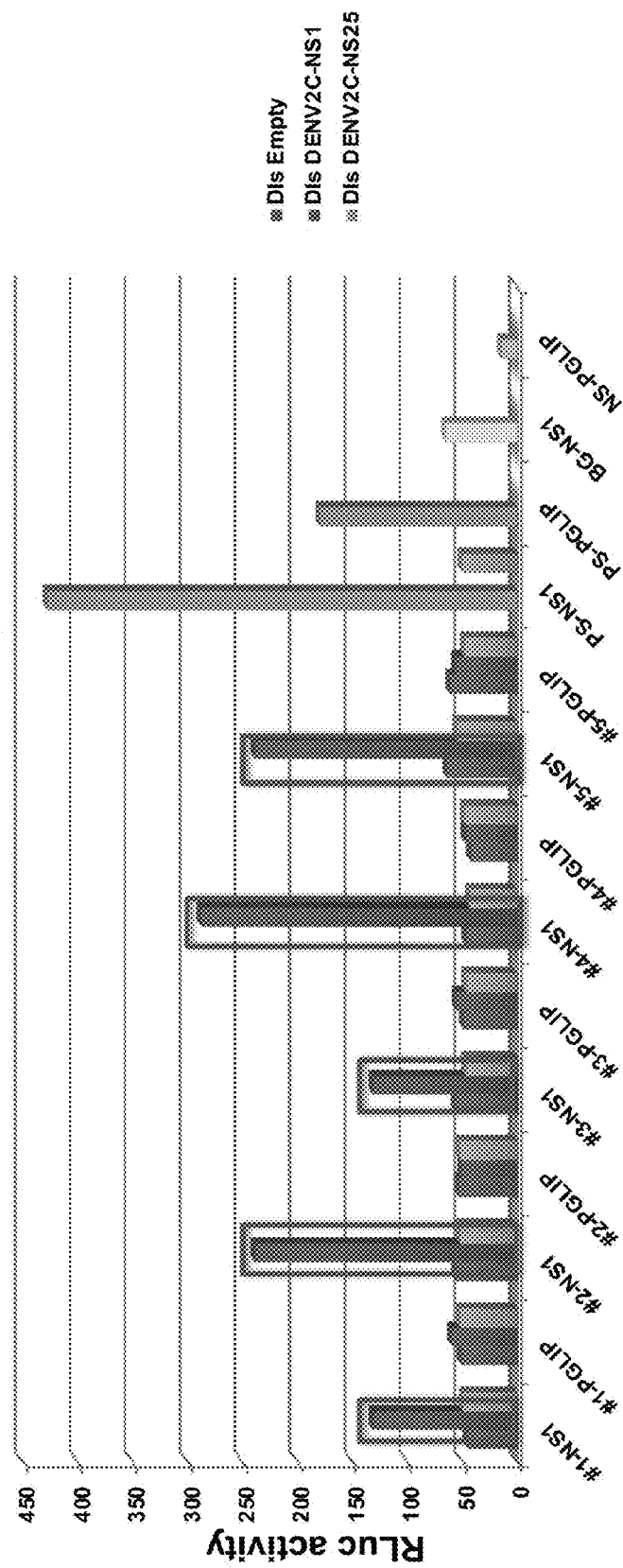

Fig. 11

Anti-NS1-GLIP antibody reaction (Week 5)

Fig. 17

SEQUENCE LISTING

<160> NUMBER OF SEQ ID NOS: 13

<210> SEQ ID NO 1
<211> LENGTH: 1140
<212> TYPE: DNA
<213> ORGANISM: Dengue virus 2

<400> SEQUENCE: 1

```
gccttggcga tgagcacctc tctgtctgtg tcactagtat tagtggggat cgtgacattg      60
tatttgggag tcatggtgca ggccgatagt ggttgcgttg tgagttggaa aaacaaagaa     120
ctgaaatgtg gtagtgggat ttttatcaca gacaacgtgc acacatggac agaacaatac     180
aaattccaac cagaatcccc ttcaaagctg gcttcagcta ccagaaggc  tcatgaagag     240
ggcatttgtg gaatccgctc agtaacaaga ttggagaatc tgatgtggaa acaaataaca     300
ccagaactga atcacattct atcagaaaat gaggtaaaat tgactatcat gacaggagac     360
attaaaggaa tcatgcaggc aggaaaacga tccctgcggc ctcaacccac tgagctgaaa     420
tactcttgga aagcatgggg caaagcgaaa atgctctcca cagagcttca taaccacacc     480
tttctcattg atggccccga acagcagaa  tgtcccaaca caaacagagc ttggaactca     540
ctagaagttg aagactatgg cttttggagta ttcaccacca acatatggct gaaactgaaa     600
gaaaggcagg atgtattttg tgactcaaaa ctcatgtcag cagccataaa agacaacagg     660
gccgtccacg ccgatatggg ttattggata gaaagcgcac ttaatgacac atggaagatt     720
gagaaagcct cctttattga agttaaaagc tgccactggc caaagtcaca cactctctgg     780
agtaatggag tgctagaaag tgagatgata attccaaaga attttgcagg accagtgtca     840
cagcacaact acagaccggg ctatcataca caaacggcag accctggca  tctaggtaaa     900
cttgagatga ctttgatttt ctgcgaagga ccacagtgg  tagtgactga ggactgtgga     960
aatagaggac cctctttaag aacaactact gcttctggaa aactcataac agaatggtgc    1020
tgccgatctt gcacattacc accgctaagg tacagaggtg aggatggatg ctggtatgga    1080
atggaaatca ggccattgaa agagaaagaa gagaacttgg tcaactcttt ggtcacagcc    1140
```

<210> SEQ ID NO 2
<211> LENGTH: 6804
<212> TYPE: DNA
<213> ORGANISM: Dengue virus 2

<400> SEQUENCE: 2

```
gccttggcga tgggacatgg gcagattgac aacttctcac taggagtctt gggaatggca      60
tgttcctgg  aagaaatgct caggacccgc gtaggaacga acatgcaat  attgctagtt     120
gcagtttctt tcgtgacatt gatcacaggg aacatgtctt ttcgagattt ggggagagtg     180
atggttatgg tgggcgctac tatgacggat gacataggca tgggcgtgac ttatcttgcc     240
ctattagcag ccttcaaagt cagaccaact tttgcagctg gactactctt gagaaagctg     300
acctccaagg aattaatgat gaccaccata ggaatcgtac tcctctctca gagcaccata     360
ccagagacta tacttgaact gactgacgcg ctggcttttgg ggatgatggt tctcaagata     420
gtgagaaata tggaaaagta tcaactagca gtgactatca tggccatctt gtgcgtccca     480
aatgcagtga tattacaaaa cgcatggaaa gtgagctgca caacactggc agtggtgtcc     540
gtttccccat tgctttttaac atcctcacag cagaaagcag attggatacc actggcgttg     600
acgatcaaag gcctcaatcc aacagccatt ttcttaacaa ccctctcaag aactagcaag     660
aaaaggagct ggccactaaa tgaggctatt atggcagtcg gatggtgag  cattttagcc     720
agttctctct taagaatga  tattcccatg acaggaccat tagtagctgg agggcttctc    780
actgtgtgtt acgtgctcac tggaagatcg gctgatttgg aactggagag agctgctgac    840
gtaagatggg aagaacaggc agagatatca ggaagtagtc caattctgtc agtaacaata    900
tcggaagatg gtagcatgtc gataaaaaat gaagaagaag  acaaacact gaccatactc    960
```

```
attaggacag gactgctggt gatatcagga cttttttcccg tgtcaatacc aatcacggca   1020
gctgcatggt acctgtggga agtgaaaaaa caacgagccg gagtattgtg ggatgtccct   1080 tcaccccac  ctgtgggaaa ggccgaactg gaagatggag cctatagaat caagcagaaa   1140
gggattctag gatactcgca gatcggagct ggagtttaca agaaggaac  attccacaca   1200 atgtggcacg tcacacgcgg tgctgtccta atgcataaag gaagagaat  tgaaccatca   1260 tgggcggacg tcaagaaaga cctaatatcg tatggaggag ctggaagct  agaaggagaa   1320 tggaaggaag gagaagaagt ccaggtcctg gcattagagc ctggaaagaa tccaagagcc   1380
gtccaaacaa aacccggtct cttcaaaact aacactggaa ccataggtgc cgtatctctg   1440 gactttttctc ctggaacgtc aggatctcca atcgtcgaca aaaaggaaa  agttgtgggc   1500 ctttatggca acggtgtcgt cacaaggagt ggaacatatg tgagtgctat agcccagact   1560
gaaaaaagca tcgaagacaa tccagagatt gaagatgaca tctttcgaaa gaaaagattg   1620
accatcatgg acctccaccc aggggcggga aaaacgaaga gataccttcc agcaatagtc   1680
agagaagcca taaaacgagg cttgaggaca ctaattctgg cccccactag agttgtggcg   1740
gctgaaatgg aagaagctct cagaggactt ccaataagat accaaacccc cgccatcaga   1800
gctgaacaca ctggacggga gattgtggat ctaatgtgtc acgccacatt taccatgagg   1860
ctgctatccc caattagagt accaaattac aacctgatca tcatggatga agcccatttc   1920
acagacccag caagcatagc agctagagga tacatttcaa ctcgagttga gatgggtgaa   1980
gcagctggga ttttcatgac agctactcct cctggaagca gagacccatt tcctcagagc   2040
aatgcaccaa tcatggatga agaaagggaa atccctgagc gttcgtggaa ttctggacat   2100
gaatgggtta cggatttttaa agggaagact gtttggtttg ttccaagtat aaaagcagga   2160
aatgatatag cagcttgcct gagaaagaat ggaaagaaag tgatacaact cagcaggaag   2220
acctttgatt ctgaatatgt caagactagg accaatgatt gggactttgt ggtcacgaca   2280
gacatttcag aaatgggcgc taacttcaag gctgagaggg ttatagaccc caggcgctgc   2340
atgaaaccag tcatactaac agacggtgaa gagcgggtga tcctggcagg acccatgcca   2400
gtgacccact ctagtgcagc acaaagaaga ggaagagtag aagaaatcc  aaaaaatgaa   2460 aatgaccagt acatatacat gggggaacct ctggaaaatg atgaagattg tgcacactgg   2520
aaagaagcta aaatgcttct agataacatc aacacgcctg aaggaatcat tcccagtatg   2580
ttcgaaccag agcgtgaaaa ggtggatgcc attgatggtg aataccgctt aagaggagaa   2640
gcgaggaaaa cttttgtgga cctaatgaga agaggagacc taccagtctg gctagcctac   2700
agagtggcag ctgaaggtat caactacgca gacagaagat ggtgctttga tggagtcaag   2760
aacaatcaaa tcttggaaga aaatgtgaa  gtggaaattt ggacaaaaga aggagaaagg   2820
aagaaattaa aacccagatg gttggatgct aggatctact ctgacccact ggcgctcaaa   2880
gaattcaagg aattcgcagc tggaagaaag tccctgaccc tgaatctaat cacagagatg   2940
ggtaggctcc caaccttcat gacccagaaa gcaaggaacg cactagacaa cttagcagtc   3000
ctgcatacgg ctgaagcagg cggaagggcg tacaatcatg ctcttagtga actgccggag   3060
accttggaga cattgcttttt actgacactc ttggccacag tcacgggcgg aatcttccta   3120
ttcttgatga gcggaaaagg catagggaag atgaccctgg gaatgtgctg cataatcacg   3180
gccagtgttc tcctatggta tgcacaaata cagccacact ggatagcagc ttcaataata   3240
ctggagtttt ttctcatagt cttgctcatt ccagaaccag aaaagcagag aacaccccaa   3300
```

-continued

```
gataaccaat taacttatgt tgtcatagcc atccttacag tggtggccgc aactatggca    3360
aacgagatgg gttccctgga aaaacaaag aaagatttcg gattgggaag cattgcaacc    3420
cagcaacctg agagcaacat cctggacata gatctacgtc ctgcatcagc ttggactcta    3480
tatgctgtgg caacaacttt catcacacca atgctgagac acagcattga aaattcctca    3540
gtgaatgtgt ctctaacggc cattgccaac caagccacag ttttaatggg tcttgggaaa    3600
ggatggccat tgtcaaaaat ggacatcgga gttcccttc tcgctatcgg gtgctattca    3660
caagttaacc ccataactct cacggcagcc cttctcttat tggtagcaca ttatgccatc    3720
ataggggcctg gactccaagc gaaagcaact agagaagctc agaaaagagc agcagcgggc    3780
atcatgaaaa acccaactgt ggatggaata acagtgattg acctagatcc aatacccctat   3840
gatccaaagt ttgaaaagca gttgggacaa gtaatgctct tagtcctctg cgtgactcaa    3900
gtattgatga tgaggactac atgggctttg tgtgaggctc taaccttagc gactgggccc    3960
atctccacac tgtgggaagg aaatccaggg agattttgga atacaactat tgcagtatca    4020
atggctaaca ttttagagg gagctacctg gccggagccg acttctctt ttctatcatg    4080
aagaatacgg ccaacacaag aaggggaact ggcaacacag gagagacgct tggagaaaaa    4140
tggaaaaacc gattgaatgc attggggaag agtgaattcc agatctataa gaaaagtgga    4200
atccaggagg tggatagaac cttagcaaaa gaaggcatca aaagaggaga aacggaccat    4260
cacgctgtgt cgcgaggctc ggcgaaactg agatggttcg tcgagagaaa cctggtcaca    4320
ccagaaggga agtagtgga cctcggttgc ggcaggggg gctggtcata ctattgtggg    4380
ggactaaaga atgtaaaaga agtcaaaggc ctaacaaaag gaggaccagg acacgaagaa    4440
cccattccca tgtcaacata tggttggaac ctggtgcgtc ttcaaagtgg agttgatgtt    4500
tttttactc cgccagaaaa gtgtgacaca ctactgtgtg acataggga gtcgtcacca    4560
aaccccacgg tcgaggcagg acgaacactc agagttctaa acctagtgga aaattggctg    4620
aacaacaaca cccaattttg catcaaggtt ctcaacccat atatgccctc agttatagaa    4680
aaaatggaag cgctgcaaag gaaatacgga ggagctttgg tgaggaatcc actctcacga    4740
aattccacac acgagatgta ctgggtatcc aatgcttccg ggaacatagt gtcatcagtg    4800
aacatgattt caagaatgtt gattaacaga ttcacaatga gacataagaa ggccacatac    4860
gagccagatg ttgacctcgg aagcggaacc cgcaacatcg gaattgaaag tgagatacca    4920
aatttggaca taattgggaa aagaatagaa aaaataaaac aagagcatga acatcatgg    4980
cactatgacc aagaccaccc atacaaaacg tgggcctacc atggcagcta cgaaacaaaa    5040
cagactggat cggcatcatc catggtgaac ggagtggtta ggctgctaac aaaaccttgg    5100
gacgtcatcc ctatggtgac acagatggca atgacagaca cgactccatt tggacaacag    5160
cgcgttttca aagagaaagt ggacacgaga acccaagaac cgaaagaagg cacgaaaaaa    5220
ctaatgaaaa tcacggcaga atggctctgg aaagaactag aaagaaaaa gacacctagg    5280
atgtgcacca gagaggaatt cacaagaaag gtgagaagca atgcagcctt aggtgccata    5340
ttcactgatg agaacaagtg gaagtcggca cgtgaggctg ttgaagatag tggattttgg    5400
gaactggttg acaaggaaag gaatcttcat cttgaaggaa agtgtgagac atgtgtgtac    5460
aacatgatgg gaaagagaga gaagaagcta ggggagttcg gcaaagcaaa aggcagcaga    5520
gccatatggt acatgtggct tggagcacgc ttcttagagt ttgaagccct aggattcttg    5580
aatgaagatc actggttttc cagagagaac tccctgagtg gagtggaagg agaagggctg    5640
cacaaactag gctacatttt aagagacgtg agcaagaaag aaggaggagc aatgtacgcc    5700
```

```
gatgacaccg caggatggga cacaaggatc acactggagg acttaaaaaa tgaagaaatg      5760
gtgacaaacc acatggaagg agaacacaag aaacttgctg aagccatttt caaattaacg      5820
taccaaaaca aggtggtgcg tgtgcaaaga ccaacaccaa gaggcacagt aatggacatt      5880
atatcaagaa gagaccaaag aggtagcgga caagttgtca cctacggcct caatactttc      5940
accaacatgg aagcccaact gatcagacag atggagggag aaggaatctt caaaagcatc      6000
cagcacctga cagtcacaga agaaattgca gtgaaaaact ggttagcaag agtgggcgt      6060 gagaggttat caagaatggc tatcagtgga gatgattgtg ttgtgaaacc cttagatgac      6120
aggtttgcaa gcgctctaac agctctaaat gacatgggaa aagttaggaa agacatacaa      6180
caatgggaac cttcaagagg atggaacgat tggacacaag tgccctttg ttcacaccat      6240 ttccatgagt taatcatgaa ggacggtcgt gtactcgtag ttccatgcag aaaccaagat      6300
gaactgattg gtagggcccg aatttcccag ggagccgggt ggtctttgcg ggaaacggcc      6360
tgtttgggga agtcttacgc ccaaatgtgg agcctgatgt acttccacag acgtgacctt      6420
aggctggcgg caaatgccat tgctcggca gtcccatcac attgggttcc aacaagtcga      6480
acaacttggt ccatacatgc cacacatgag tggatgacaa cagaagatat gctgacagtc      6540
tggaacaggg tgtggattca agaaaaccca tggatggaag acaaaactcc agtagaatca      6600
tgggaggaaa tcccatattt ggggaaaaga gaagaccaat ggtgcggctc actgatcggg      6660
ctaacaagca gggccacctg gcaaagaac atccaaacag caataaatca agttagatcc      6720
ctaataggca atgaggaata cacagactac atgccatcca tgaaaaggtt cagaagagaa      6780
gaggaagagg caggagtcct gtgg                                             6804
```

<210> SEQ ID NO 3
<211> LENGTH: 6804
<212> TYPE: DNA
<213> ORGANISM: Artificial
<220> FEATURE:
<223> OTHER INFORMATION: Modified DNA

<400> SEQUENCE: 3

```
gccttggcga tgggacatgg gcagattgac aacttctcac taggagtctt gggaatggca       60
ttgttcctgg aagaaatgct caggacccgc gtaggaacga acatgcaat attgctagtt       120 gcagtttctt tcgtgacatt gatcacaggg acatgtcctt ttcgagattt ggggagagtg      180
atggttatgg tgggcgctac tatgacggat gacataggca tgggcgtgac ttatcttgcc      240
ctattagcag ccttcaaagt cagaccaact tttgcagctg actactctt gagaaagctg      300 acctccaagg aattaatgat gaccaccata ggaatcgtac tcctctctca gagcaccata      360
ccagagacta tacttgaact gactgacgcg ctggctttgg ggatgatggt tctcaagata      420
gtgagaaata tggaaaagta tcaactagca gtgactatca tggccatctt gtgcgtccca      480
aatgcagtga tattacaaaa cgcatggaaa gtgagctgca caacactggc agtggtgtcc      540
gtttccccat tgctttaac atcctcacag cagaaagcag attggatacc actggcgttg      600
acgatcaaag gcctcaatcc aacagccatt ttcttaacaa ccctctcaag aactagcaag      660
aaaaggagct ggccactaaa tgaggctatt atggcagtcg ggatggtgag cattttagcc      720
agttctctct taagaatga tattcccatg acaggaccat tagtagctgg agggcttctc      780
actgtgtgtt acgtgctcac tggaagatcg gctgatttgg aactggagag agctgctgac      840
gtaagatggg aagaacaggc agagatatca ggaagtagtc caattctgtc agtaacaata      900
```

```
tcggaagatg gtagcatgtc gataaaaaat gaagaagaag aacaaacact gaccatactc    960
attaggacag gactgctggt gatatcagga ctttttcccg tgtcaatacc aatcacggca   1020
gctgcatggt acctgtggga agtgaaaaaa caacgagccg gagtattgtg ggatgtccct   1080 tcaccccac ctgtgggaaa ggccgaactg gaagatggag cctatagaat caagcagaaa   1140
gggattctag atactcgca gatcggagct ggagtttaca agaaggaac attccacaca   1200 atgtggcacg tcacacgcgg tgctgtccta atgcataaag ggaagagaat tgaaccatca   1260
tgggcggacg tcaagaaaga cctaatatcg tatggaggag gctggaagct agaaggagaa   1320
tggaaggaag gagaagaagt ccaggtcctg gcattagagc ctggaaagaa tccaagagcc   1380
gtccaaacaa aacccggtct cttcaaaact aacactggaa ccataggtgc cgtatctctg   1440
gacttttctc ctggaacgtc aggatctcca atcgtcgaca aaaaggaaa agttgtgggc   1500 ctttatggca acggtgtcgt cacaaggagt ggaacatatg tgagtgctat agcccagact   1560 gaaaaagca tcgaagacaa tccagagatt gaagatgaca tctttcgaaa gaaaagattg   1620
accatcatgg acctccaccc aggggcggga aaaacgaaga gataccttcc agcaatagtc   1680
agagaagcca taaacgagg cttgaggaca ctaattctgg ccccactag agttgtggcg   1740 gctgaaatgg aagaagctct cagaggactt ccaataagat accaaccccc cgccatcaga   1800
gctgaacaca ctggacggga gattgtggat ctaatgtgtc acgccacatt taccatgagg   1860
ctgctatccc caattagagt accaaattac aacctgatca tcatggatga agcccatttc   1920
acagacccag caagcatagc agctagagga tacatttcaa ctcgagttga gatgggtgaa   1980
gcagctggga ttttcatgac agctactcct cctggaagca gagacccatt tcctcagagc   2040
aatgcaccaa tcatggatga agaaagggaa atccctgagc gttcgtggaa ttctggacat   2100
gaatgggtta cggattttaa agggaagact gttttggttttg ttccaagtat aaaagcagga   2160
aatgatatag cagcttgcct gagaaagaat ggaaagaaag tgatacaact cagcaggaag   2220
acctttgatt ctgaatatgt caagactagg accaatgatt gggacttttgt ggtcacgaca   2280 gacatttcag aaatgggcgc taacttcaag gctgagaggg ttatagaccc caggcgctgc   2340
atgaaaccag tcatactaac agacggtgaa gagcgggtga tcctggcagg acccatgcca   2400
gtgacccact ctagtgcagc acaaagaaga ggaagagtag aagaaatcc aaaaaatgaa   2460 aatgaccagt acatatacat gggggaacct ctggaaaatg atgaagattg tgcacactgg   2520
aaagaagcta aaatgcttct agataacatc aacacgcctg aaggaatcat tcccagtatg   2580
ttcgaaccag agcgtgaaaa ggtggatgcc attgatggtg aataccgctt aagaggagaa   2640
gcgaggaaaa cttttgtgga cctaatgaga agaggagacc taccagtctg gctagcctac   2700 cagagtggcag ctgaaggtat caactacgca gacagaagat ggtgctttga tggagtcaag   2760
aacaatcaaa tcttggaaga aaatgtggaa gtggaaattt ggacaaaaga aggagaaagg   2820
aagaaattaa aacccagatg gttggatgct aggatctact ctgacccact ggcgctcaaa   2880
gaattcaagg aattcgcagc tggaagaaag tccctgaccc tgaatctaat cacagagatg   2940
ggtaggctcc caaccttcat gacccagaaa gcaaggaacg cactagacaa cttagcagtc   3000
ctgcatacgg ctgaagcagg cggaagggcg tacaatcatg ctcttagtga actgccggag   3060
accttggaga cattgctttt actgacactc ttggccacag tcacgggcgg aatcttccta   3120
ttcttgatga gcggaaaagg catagggaag atgaccctgg gaatgtgctg cataatcacg   3180
gccagtgttc tcctatggta tgcacaaata cagccacact ggatagcagc ttcaataata   3240
ctggagtttt ttctcatagt cttgctcatt ccagaaccag aaaagcagag aacaccccaa   3300
```

```
gataaccaat taacttatgt tgtcatagcc atccttacag tggtggccgc aactatggca    3360
aacgagatgg gtttcctgga aaaacaaag aaagatttcg gattgggaag cattgcaacc    3420
cagcaacctg agagcaacat cctggacata gatctacgtc ctgcatcagc ttggactcta    3480
tatgctgtgg caacaacttt catcacacca atgctgagac acagcattga aaattcctca    3540
gtgaatgtgt ctctaacggc cattgccaac caagccacag ttttaatggg tcttgggaaa    3600
ggatggccat tgtcaaaaat ggacatcgga gttccccttc tcgctatcgg gtgctattca    3660
caagttaacc ccataactct cacggcagcc cttctcttat tggtagcaca ttatgccatc    3720
atagggcctg gactccaagc gaaagcaact agagaagctc agaaaagagc agcagcgggc    3780
atcatgaaaa acccaactgt ggatggaata acagtgattg acctagatcc aatacccta t    3840 gatccaaagt ttgaaaagca gttgggacaa gtaatgctct tagtcctctg cgtgactcaa    3900
gtattgatga tgaggactac atgggctttg tgtgaggctc taaccttagc gactgggccc    3960
atctccacac tgtgggaagg aaatccaggg agattttgga atacaactat tgcagtatca    4020
atggctaaca ttttagagg gagctacctg gccggagccg gacttctctt ttctatcatg    4080
aagaatacgg ccaacacaag aaggggaact ggcaacacag gagagacgct ggagaaaaa    4140 tggaaaaacc gattgaatgc attggggaag agtgaattcc agatctataa gaaaagtgga    4200
atccaggagg tggatagaac cttagcaaaa gaaggcatca aagaggaga acgaccat    4260 cacgctgtgt cgcgaggctc ggcgaaactg agatggttcg tcgagagaaa cctggtcaca    4320
ccagaaggga aagtagtgga cctcggttgc ggcaggggg gctggtcata ctattgtggg    4380
ggactaaaga atgtaaaaga agtcaaaggc ctaacaaaag gaggaccagg acacgaagaa    4440
cccattccca tgtcaacata tggttggaac ctggtgcgtc ttcaaagtgg agttgatgtt    4500
ttttttactc cgccagaaaa gtgtgacaca ctactgtgtg acataggggga gtcgtcacca    4560 aaccccacgg tcgaggcagg acgaacactc agagttctaa acctagtgga aaattggctg    4620
aacaacaaca cccaatttg catcaaggtt ctcaacccat atatgccctc agttatagaa    4680 aaaatgaag cgctgcaaag gaaatacgga ggagctttgg tgaggaatcc actctcacga    4740
aattccacac acgagatgta ctgggtatcc aatgcttccg ggaacatagt gtcatcagtg    4800
aacatgattt caagaatgtt gattaacaga ttcacaatga gacataagaa ggccacatac    4860
gagccagatg ttgacctcgg aagcggaacc cgcaacatcg gaattgaaag tgagatacca    4920
aatttggaca taattgggaa aagaatagaa aaaataaaac aagagcatga aacatcatgg    4980
cactatgacc aagaccaccc atacaaaacg tgggcctacc atggcagcta cgaaacaaaa    5040
cagactggat cggcatcatc catggtgaac ggagtggtta ggctgctaac aaaaccttgg    5100
gacgtcatcc ctatggtgac acagatggca atgacagaca cgactccatt tggacaacag    5160
cgcgttttca agagaaagt ggacacgaga acccaagaac cgaaagaagg cacgaaaaaa    5220
ctaatgaaaa tcacggcaga atggctctgg aagaactag aaagaaaaa gacacctagg    5280 atgtgcacca gagaggaatt cacaagaaag gtgagaagca atgcagcctt aggtgccata    5340
ttcactgatg agaacaagtg gaagtcggca cgtgaggctg ttgaagatag tggattttgg    5400
gaactggttg acaaggaaag gaatcttcat cttgaaggaa agtgtgagac atgtgtgtac    5460
aacatgatgg gaaagagaga aaagaagcta ggggagttcg gcaaagcaaa aggcagcaga    5520
gccatatggt acatgtggct tggagcacgc ttcttagagt ttgaagccct aggattcttg    5580
aatgaagatc actggttttc cagagagaac tccctgagtg gagtggaagg agaagggctg    5640
```

```
cacaaactag gctacatttt aagagacgtg agcaagaaag aaggaggagc aatgtacgcc    5700
gatgacaccg caggatggga cacaaggatc acactggagg acttaaaaaa tgaagaaatg    5760
gtgacaaacc acatggaagg agaacacaag aaacttgctg aagccatttt caaattaacg    5820
taccaaaaca aggtggtgcg tgtgcaaaga ccaacaccaa gaggcacagt aatggacatt    5880
atatcaagaa gagaccaaag aggtagcgga caagttgtca cctacggcct caatactttc    5940
accaacatgg aagcccaact gatcagacag atggagggag aaggaatctt caaaagcatc    6000
cagcacctga cagtcacaga agaaattgca gtgaaaaact ggttagcaag agtggggcgt    6060
gagaggttat caagaatggc tatcagtgga aatgattgtg ttgtgaaacc cttagatgac    6120
aggtttgcaa gcgctctaac agctctaaat gacatgggaa aagttaggaa agacatacaa    6180
caatgggaac cttcaagagg atggaacgat tggacacaag tgcccttttg ttcacaccat    6240
ttccatgagt taatcatgaa ggacggtcgt gtactcgtag ttccatgcag aaaccaagat    6300
gaactgattg gtagggcccg aatttcccag ggagccgggt ggtctttgcg ggaaacggcc    6360
tgtttgggga agtcttacgc ccaaatgtgg agcctgatga cttccacag acgtgacctt    6420 aggctggcgg caaatgccat ttgctcggca gtcccatcac attgggttcc aacaagtcga    6480
acaacttggt ccatacatgc cacacatgag tggatgacaa cagaagatat gctgacagtc    6540
tggaacaggg tgtggattca agaaaaccca tggatggaag acaaaactcc agtagaatca    6600
tgggaggaaa tcccatattt ggggaaaaga gaagaccaat ggtgcggctc actgatcggg    6660
ctaacaagca gggccacctg ggcaaagaac atccaaacag caataaatca agttagatcc    6720
ctaataggca atgaggaata cacagactac atgccatcca tgaaaaggtt cagaagagaa    6780
gaggaagagg caggagtcct gtgg                                          6804

<210> SEQ ID NO 4
<211> LENGTH: 122
<212> TYPE: DNA
<213> ORGANISM: Artificial
<220> FEATURE:
<223> OTHER INFORMATION: Synthetic DNA

<400> SEQUENCE: 4
gggcggccct gcaggaaaaa ttgaaaataa atacaaaggt tcttgagggt tgtgttaaat      60
tgaaagcgag aaataatcat aaatagcctt ggcgatgagc acctctctgt ctgtgtcact    120
ag                                                                    122

<210> SEQ ID NO 5
<211> LENGTH: 48
<212> TYPE: DNA
<213> ORGANISM: Artificial
<220> FEATURE:
<223> OTHER INFORMATION: Synthetic DNA

<400> SEQUENCE: 5
gggcggcgcg atcgctcact attaggctgt gaccaaagag ttgaccaa                   48

<210> SEQ ID NO 6
<211> LENGTH: 118
<212> TYPE: DNA
<213> ORGANISM: Artificial
<220> FEATURE:
<223> OTHER INFORMATION: Synthetic DNA

<400> SEQUENCE: 6
gggcggccct gcaggaaaaa ttgaaaataa atacaaaggt tcttgagggt tgtgttaaat      60
```

```
tgaaagcgag aaataatcat aaatagcctt ggcgatggga catgggcaga ttgacaac      118
```

<210> SEQ ID NO 7
<211> LENGTH: 46
<212> TYPE: DNA
<213> ORGANISM: Artificial
<220> FEATURE:
<223> OTHER INFORMATION: Synthetic DNA

<400> SEQUENCE: 7

```
gggcggcgcg atcgctcaca tttaccacag gactcctgcc tcttcc                   46
```

<210> SEQ ID NO 8
<211> LENGTH: 40
<212> TYPE: DNA
<213> ORGANISM: Artificial
<220> FEATURE:
<223> OTHER INFORMATION: Synthetic DNA

<400> SEQUENCE: 8

```
caagaatggc tatcagtgga atgattgtg ttgtgaaacc                           40
```

<210> SEQ ID NO 9
<211> LENGTH: 40
<212> TYPE: DNA
<213> ORGANISM: Artificial
<220> FEATURE:
<223> OTHER INFORMATION: Synthetic DNA

<400> SEQUENCE: 9

```
ggtttcacaa cacaatcatt tccactgata gccattcttg                          40
```

<210> SEQ ID NO 10
<211> LENGTH: 1485
<212> TYPE: DNA
<213> ORGANISM: Dengue virus 1

<400> SEQUENCE: 10

```
atgcgatgcg tgggaatagg cagcagggac ttcgtggaag gactgtcagg agcaacttgg    60
gtagatgtgg tactggaaca tggaagttgc gtcaccacca tggcaaaaga caaaccaaca   120
ctggacattg aactcttgaa gacggaagtc acaaaccctg ccgtcctgcg caaactttgc   180
attgaagcta aatatcaaa caccaccact gactcaagat gtccaacaca aggagaagcc   240
acactggtgg aagaacaaga cgcgaacttt gtgtgtcgac gaacgtttgt ggacagaggc   300
tggggcaatg gctgtgggct cttcggaaaa ggaagcctac taacgtgtgc taagtttaag   360
tgtgtgacaa aactggaagg aaagatagtt caatatgaaa acttgaaata ttcagtaata   420
gtcaccgttc acactggaga ccagcatcag gtgggaaatg aaagcacaga acatgggaca   480
actgcaacta aacacctca agctcctacg acggaaatac agctgaccga ctacggagct   540
cttacattgg attgttcacc tagaacagga ttagacttca atgaaatggt gttgttgaca   600
atgaaagaaa aatcatggct agtccacaaa caatggttc tagacttacc actgccttgg   660
acctcgggag cttcaacatc acaagagact tggaacagac aagatttgct ggtgacattt   720
aagacagctc atgcaaagaa gcaggaagta gtcgtactag gatcacaaga aggagcaatg   780
cacactgcgt tgaccggagc gacagaaatc caaacgtctg gaacgacaac aatttttgca   840
ggacacttga atgtgtagact aaagatggac aaactgactc taaagggat gtcatatgtg   900
atgtgcacag gctcattcaa gctagagaaa gaagtggctg agacccagca tggaactgtt   960
```

| | |
|---|---|
| ctagtgcaga ttaaatacga aggaacagat gcaccatgca agattccttt tttgacccaa | 1020 |
| gatgaaaaag gagtaaccca gaatgggaga ttgataacag ccaaccccat agtcactgac | 1080 |
| aaagaaaaac cagtcaacat tgaggcagaa ccgccttttg gtgagagtta catcgtgata | 1140 |
| ggagcaggtg aaaaagcttt gaaactaagc tggttcaaga aaggaagcag catagggaaa | 1200 |
| atgtttgagg caactgccag aggagcacga aggatggcca tactgggaga caccgcatgg | 1260 |
| gactttggtt ctataggagg agtgttcacg tctgttggaa aattagtaca ccagattttt | 1320 |
| ggaactgcat atggagtttt gttcagcggt gtttcctgga ccatgaaaat aggaatagggg | 1380 |
| gttctgctga catggttagg attaaactca aggagcactt ccctctcgat gacgtgcatt | 1440 |
| gcagttggcc tagtaacact atacctagga gtcatggttc aggcg | 1485 |

<210> SEQ ID NO 11
<211> LENGTH: 1485
<212> TYPE: DNA
<213> ORGANISM: Dengue virus 2

<400> SEQUENCE: 11

| | |
|---|---|
| atgcgttgca taggaatatc aaatagagac tttgtagaag gggtttcagg aggaagttgg | 60 |
| gttgacatag tcttagaaca tggaagctgt gtgacaacaa tggcaaaaaa caaaccaaca | 120 |
| ttggatttcg aactgataaa aacggaagcc aaacagcctg ccaccttaag gaagtactgc | 180 |
| atagaagcaa aactaaccaa cacaacaaca gaatcccgtt gcccaacaca aggggaaccc | 240 |
| agtctaaaag aagagcagga caagaggttc gtctgcaaac actccatggt agacagagga | 300 |
| tgggggaatg gatgtggatt atttggaaag ggaggcattg tgacctgtgc tatgttcaca | 360 |
| tgcaaaaaga acatggaagg gaaaatcgtg caaccagaaa acttggaata caccattgtg | 420 |
| gtaacacctc actcagggga gagcatgcg gtcggaaatg cacaggaaa gcacggtaag | 480 |
| gaaatcaaag taacaccaca gagttccatt acagaagcag aattgacagg ttatggcacc | 540 |
| gtcacgatgg agtgctcccc gagaacaggc ctcgacttca atgagatggt gttgctgcag | 600 |
| atggaaaata aagcttggct ggtgcatagg caatggtttc tagacctgcc attaccatgg | 660 |
| ctgcccggag cggataaaca agagtccaat tggatacaga agaaacatt ggtcactttc | 720 |
| aaaaatcccc atgcgaagaa acaggatgtt gttgttttag gatcccaaga aggggccatg | 780 |
| cacacagcac tcacaggagc cacagaaatc caaatgtcgt caggaaactt gctcttcact | 840 |
| ggacatctca agtgcaggct gagaatggac aagctacagc ttaaaggaat gtcatactcc | 900 |
| atgtgcacag gaaagtttaa agttgtgaag gaaatagcag aaacacaaca tggaacgata | 960 |
| gttatcagag tgcaatatga aggggacggc tctccatgca aaatcccttt tgagataatg | 1020 |
| gatttggaaa aagatatgt cttaggccgc ctgatcacag ttaacccaat tgtaacagaa | 1080 |
| aaagatagcc cagtcaacat agaagcagaa cctccattcg agacagttta catcatcata | 1140 |
| ggagtagagc cggacaact gaagctcaac tggttcaaga aaggaagttc tatcggccaa | 1200 |
| atgtttgaga caacgatgag aggggcgaag agaatggcca ttttgggtga cacagcctgg | 1260 |
| gacttcggat ccctgggagg agtgtttaca tctataggaa aagctcttca ccaagtcttt | 1320 |
| ggagcgatct atggagctgc cttcagtggg gtttcatgga ccatgaaaat cctcatagga | 1380 |
| gtcattatca catggatagg aatgaactca cgcagcacct cactatctgt gtcactagta | 1440 |
| ctggtgggaa ttgtgacact gtatttggga gtcatggtgc aggcc | 1485 |

<210> SEQ ID NO 12
<211> LENGTH: 10680

```
<212> TYPE: DNA
<213> ORGANISM: Dengue virus 3

<400> SEQUENCE: 12
```

| | | | | | |
|---|---|---|---|---|---|
| agttgttagt | ctacgtggac | cgacaagaac | agtttcgact | cggaagcttg | cttaacgtag | 60 |
| tgctaacagt | tttttattag | agagcagatc | tctgatgaac | aaccaacgga | agaagacggg | 120 |
| aaaaccgtct | atcaatatgc | tgaaacgcgt | gagaaaccgt | gtgtcaactg | gatcacagtt | 180 |
| ggcgaagaga | ttctcaaaag | gattgctgaa | cggccaggga | ccaatgaaat | tggtcatggc | 240 |
| gttcatagcc | ttccttagat | ttctggccat | tccaccaaca | gcaggagttt | tggccagatg | 300 |
| gggaaccttc | aagaagtcgg | gggccattaa | ggtcctgaaa | ggcttcaaga | aggagatttc | 360 |
| aaacatgctg | agcataatca | acaaacggaa | aaagacatcg | ctctgtctca | tgatgatatt | 420 |
| gccagcagca | cttgctttcc | acttgacttc | acgagatgga | gagccgcgca | tgattgtggg | 480 |
| gaagaatgaa | agaggaaaat | ccctactttt | aagacagcc | tctggaatca | acatgtgcac | 540 |
| actcatagcc | atggacttgg | agagatgtgt | tgatgacacg | gtcacttaca | atgcccca | 600 |
| cattaccgag | gtgaacctg | aagacattga | ctgctggtgc | aaccttacat | caacatgggt | 660 |
| gacttatgga | acgtgcaatc | aagctggaga | gcatagacgc | gacaagagat | cagtggcgtt | 720 |
| agctccccat | gtcggcatgg | gactggacac | acgcaccca | acctggatgt | cggctgaagg | 780 |
| agcttggaga | caagtcgaga | aggtagagac | atgggcct | aggcacccag | ggttcaccat | 840 |
| actagcccta | tttcttgccc | attacatagg | cacctccttg | acccagaagg | tggttatttt | 900 |
| tatactacta | atgctggtca | ccccatccat | gacaatgaga | tgtgtgggag | tgggaaacag | 960 |
| agattttgtg | gaaggtctgt | caggagctac | gtgggttgac | gtggtgctag | agcacgggg | 1020 |
| gtgtgtgacc | accatggcta | gaacaagcc | cacgctggat | atagagcttc | agaagaccga | 1080 |
| ggccacccaa | ctggcgaccc | taaggaagct | atgcattgag | gggaaaatta | ccaacataac | 1140 |
| aactgactca | agatgtccta | cccaaggga | agcggttttg | cctgaggagc | aggaccagaa | 1200 |
| ctacgtgtgt | aagcatacat | acgtagacag | aggctgggg | aacggttgtg | gtttgtttgg | 1260 |
| caagggaagc | ttggtaacat | gtgcgaaatt | tcaatgcctg | gaaccgatag | agggaaaagt | 1320 |
| ggtgcaatat | gagaacctca | aatacaccgt | catcattaca | gtgcacacag | agaccaaca | 1380 |
| ccaggtggga | aatgaaacgc | agggagtcac | ggctgagata | acgcctcagg | catcaactac | 1440 |
| tgaagccatc | ttgcctgaat | atggaacct | tgggctagaa | tgctcaccac | ggacaggttt | 1500 |
| ggacttcaat | gaaatgatct | tactaacaat | gaagaacaaa | gcatggatgg | tacacagaca | 1560 |
| atggtttttt | gacctaccctc | taccatggac | atcaggagct | acaacagaaa | caccaacttg | 1620 |
| gaacaggaag | gagctccttg | tgacattcaa | aaatgcacat | gcgaaaaac | aagaagtagt | 1680 |
| tgtccttgga | tcgcaagagg | gagcaatgca | taccgcactg | acaggagcca | cagaaatcca | 1740 |
| aaactcagga | ggcacaagca | tttttgcggg | gcacttaaag | tgtagactta | agatggacaa | 1800 |
| attggaactc | aagggggatga | gctatgcaat | gtgcacgaat | accttttgtgt | tgaagaaaga | 1860 |
| agtctcagaa | acgcagcatg | ggacaatact | cattaaggtc | gagtacaaag | gggaagatgc | 1920 |
| accttgcaag | attcctttct | ccacagagga | tggacaaggg | aaagctcaca | atggcagact | 1980 |
| gatcacagcc | aacccagtgg | tgactaagaa | ggaggagcct | gttaacattg | aggctgaacc | 2040 |
| tccttttggg | gaaagtaata | tagtaattgg | aattggagac | aatgccttga | aaatcaactg | 2100 |
| gtacaagaag | ggaagctcta | ttgggaagat | gttcgaggcc | actgccagag | gtgcaaggcg | 2160 |
| catggccatc | ttgggagaca | cagcttggga | ctttggatca | gtgggtggtg | ttctgaactc | 2220 |

-continued

```
attaggcaaa atggtgcacc aaatattcgg aagtgcttac acagccctat tcagtggagt    2280
ctcttgggtg atgaaaattg gaataggtgt tctcttgact tggataggt tgaattcaaa     2340 aaacacatcc atgtcatttt catgcattgc gataggaatc atcacactct atctgggagc    2400
tgtggtgcaa gctgacatgg ggtgtgtcat aaactgaaaa ggcaaagaac ttaaatgcgg    2460
aagtggaatt ttcgtcacca acgaggtcca tacctggaca gagcagtaca aattccaagc    2520
agactcccca aaaagattgg cgacagccat tgcaggcgct tgggagaatg gagtgtgtgg    2580
gattaggtca acaaccagaa tggagaacct cttgtggaag caaatagcca atgaactgaa    2640
ctacatatta tgggaaaaca atatcaaact aacagtagtt gtgggcgata caattggggt    2700
cttagagcaa gggaagagaa cactaacacc acaacccatg gagctaaaat actcatggaa    2760
aacgtgggga aagcaaaaa tagtgacagc tgaaacacaa aactcctttt ttataataga    2820
cgggccaaac acaccggagt gtccaagtgc ctcaagagca tggaatgtgt gggaggtgga    2880
agattacggg ttcggagtct tcacaaccaa catatggctg aaactccgag aggtgtacac    2940
ccaactatgt gaccataggc taatgtcggc agctgtcaag gatgagaggg ccgtacatgc    3000
cgacatgggc tactggatag aaagccaaaa gaatggaagt tggaagctag aaaaagcatc    3060
cctcatagag gtaaaaacct gcacatggcc aaaatcacac actctctgga gcaacggtgt    3120
gctagagagt gacatgatca ttccaaagag tctagctggt cccatttcgc aacacaacca    3180
caggcccggg taccacaccc aaacggcagg accctggcac ttagaaaatt tggagctgga    3240
cttcacctat tgtgaaggaa caacagttgt catcacagaa aactgtggga caagaggccc    3300
atcattgaga acgacaacag tatcaggaaa gttgatacac gaatggtgtt gccgctcgtg    3360
cacacttcct cctctgcgat acatgggaga agacggctgt tggtatggca tggaaatcag    3420
acccatcagt gagaaagaag agaacatggt aaagtcttta gtctcagcgg aagtggaaa    3480 ggtagacaac ttcacaatgg gtatcttgtg cttggcaatc ctctttgaag aggtgatgag    3540
aggaaaattt gggaagaaac acatgattgc aggggtttc ttcacgtttg tgctccttct    3600
ctcagggcaa ataacatgga gagacatggc gcacacacta ataatgattg gtccaacgc    3660 ctctgacagg atgggaatgg gcgtcaccta tctagctttg attgcaacat ttaaaatcca    3720
gccattcctg gctttgggat ttttcctaag aaaactgaca tctagagaaa atttactgtt    3780
aggagttgga ctggctatgg caacaacgtt acaactgcca gaggacattg aacaaatggc    3840
aaatggaatc gccctggggc tcatggctct taaattgata acacaatttg aaacatacca    3900
attatggacg gcattaatct ccttaacgtg ttcaaataca atttcacgt tgactgttgc    3960 ctggagaaca gccaccctga ttttggccgg agtttcactt ttaccagtgt gccagtcttc    4020
gagcatgagg aaaacagact ggcttccaat gacagtggca gctatgggag tcccacccct    4080
accactcttt atttttagct tgaaagacac actcaaaagg agaagctggc cactgaatga    4140 agggtgatg gctgttgggc ttgtgagcat tcttgccagt tctctcctta gaaatgacgt    4200
acccatggct ggaccattag tggccggggg cttgctgata gcgtgctacg tcataactgg    4260
cacgtcagca gaccttacag tagaaaaagc agcagatgta acatgggagg aagaggctga    4320
gcaaacagga gtgtcccaca acttaatgat cacagttgat gatgatgaa caatgagaat    4380 aaaagatgat gagactgaga atattctaac agtgcttttg aagacagcat tactaatagt    4440
atcaggtatt tttccatact ccatacccgc aacattgttg gtctggcata cttggcaaaa    4500
gcaaacccaa agatccggtg ttctatggga cgtacccagc cccccagaga cacagaaagc    4560
agaactggaa gaagggggtct ataggatcaa acagcaagga attcttggga aaacccaagt    4620
```

```
aggggttgga gtacaaaaag aaggagtctt ccacaccatg tggcacgtca caagagggc    4680
agtgttgaca cataatggga aaagactgga accaaactgg gctagcgtga aaaaagatct   4740
gatttcatac ggaggaggat ggagattgag cgcacaatgg caaaggggg aggaggtgca    4800
ggttattgcc gtagagcccg ggaagaaccc aaagaacttt caaaccatgc caggcacatt   4860
tcagactaca acaggggaaa taggagcaat tgcactggat ttcaagcctg aacttcagg    4920
gtctcctatc ataaacagag agggaaaggt agtgggacta tatggcaatg gagtggttac   4980
aaagaatggc ggctacgtca gcggaatagc gcaaacaaat gcagaaccag atggaccgac   5040
gccagagttg gaagaagaga tgttcaaaaa gcgaaatcta accataatgg atcttcatcc   5100
tgggtcagga aagacacgga aataccttcc agccattgtt agagaggcaa tcaagagacg   5160
tttaagaact ctaatttgg caccgacaag ggtggttgca gctgagatgg aagaagcatt    5220
gaaaggctc ccaataaggt accaaacaac agcaacaaaa tctgaacaca caggaagaga    5280
gattgttgat ctaatgtgcc acgcaacgtt cacaatgcgt ctgctgtcac cagttagggt   5340
tccaaattat aacttgataa taatggatga ggcccatttc acagacccag ccagtatagc   5400
ggccagaggg tacatatcaa ctcgtgttgg aatgggagag gcagccgcaa ttttcatgag   5460
tgcaacgccc cctggaacag ctgatgcctt tcctcagagc aatgctccaa ttcaagatga   5520
agaaagggac ataccagaac gctcatggaa ttcaggcaat gaatggatta ccgacttcgc   5580
cgggaaaacg gtgtggtttg tccccagcat caaagccgga aatgacatag caaactgctt   5640
gcgaaagaac gggaaaaagg tcattcaact tagtaggaag acttttgata cagaatatca   5700
gaagactaaa ctaaatgatt gggactttgt ggtgacaact gacatttcag aaatgggggc   5760
caatttcaaa gcagatagag tgatcgaccc aagaagatgt ctaaaaccag tgatcctgac   5820
agatggacca gagcgggtga tcttggctgg accaatgcca gtcaccgcgg cgagtgctgc   5880
gcaaaggaga gggagagttg gcaggaaccc acaaaaagaa aatgaccagt acatattcac   5940
gggccagcct ctcaacaatg atgaagacca tgctcactgg acagaagcaa aatgttgct   6000
ggacaacatc aacactccag aaggaatcat accagctctc tttgaaccag aaagggagaa   6060
gtcagccgcc atagacggtg aatatcgcct gaaggggtgaa tccaggaaga ctttcgtgga   6120
actcatgagg agggggtgacc ttccagtttg gttagcccac aaagtagcat cagaagggat   6180
caaatataca gataggaaat ggtgctttga tggacagcgc aacaatcaaa ttttagagga   6240
aaacatggac gtggaaatct ggacaaagga aggagaaaag aaaaaattga gacctaggtg   6300
gcttgatgcc cgcacttatt cagatccctt agcactcaag gaattcaagg actttgcggc   6360
tggcagaaag tcaattgccc ttgatcttgt gacagaaata ggaagagtgc cttcacacct   6420
agccacagaa acgagaaacg ctctggacaa tctggtgatg ctgcacacgt cagaacatgg   6480
cggtagggcc tacaggcatg cggtggagga actaccagaa acaatggaaa cactcctact   6540
cttgggactc atgatcttac tgacaggtgg agcaatgctt tcttgatat caggtaaagg   6600
gattggaaag acttcaatag gactcatttg tgtgattgct tccagcggca tgctgtggat   6660
ggccgaaatc ccactccaat ggatcgcgtc ggctatagtc ctggagtttt ttatgatggt   6720
gttgcttata ccagaaccag aaaagcgagg accccccaa gacaaccaac tcgcatatgt   6780
cgtaataggc atacttacat tggctgcaat aatagcggcc aatgaaatgg actgttgga   6840
aactacaaag agagatttag gaatgtctaa ggagcccggt gttgtttctc caactagcta   6900
tttggatgtg gacttgcacc cagcatcagc ctggacatta tacgccgtgg ccactacagt   6960
```

```
aataacacca atgttaagac ataccataga gaattctaca gcaaatgtgt ccctggcagc    7020
tatagccaac caggcagtgg tcctgatggg tttggacaaa ggatggccaa tatcaaaaat    7080
ggacttaggc gtaccactac tggcattggg ttgctattca caagtgaacc cactgactct    7140
aacagcggca gtactttgc taattacaca ttatgctatt ataggtccag gactgcaggc     7200
aaaagccact cgtgaagctc aaaaaaggac agctgctgga ataatgaaga atccaacggt    7260
ggatgggata ataacgatag acctagatcc tgtaatatac gattcaaaat ttgaaaagca    7320
actgggacag gtcatgctcc tggttttgtg tgcagttcaa ctgttgttaa tgagaacatc    7380
atgggccttg tgtgaagctt taactttagc tacaggacca ataacaacac tctgggaagg    7440
atcacctggg aagttttgga ataccacgat agctgtttcc atgcgaaaca tttttagagg    7500
gagctattta gcaggagctg ggcttgcctt ttctattatg aaatcagttg gaacaggaaa    7560
aagaggaaca ggctctcaag gtgaaacttt aggagaaaaa tggaaaaaga aattgaatca    7620
attatcccgg aaaagttttg accttacaa gaagtctgga atcactgaag tggatagaac     7680
agaagccaaa aagggttga aaagaggaga acaacacat catgccgtgt ctagaggtag      7740
tgcaaaactt caatggttag tggagagaaa catggtcatt cccgaaggaa gagtcataga    7800
cctgggctgt ggaagaggag gctggtcata ttactgtgca ggactgaaaa aagtcacaga    7860
agtgcgagga tacacaaaag gcggtccagg acacgaagaa ccagtgccta tgtcaacata    7920
tggatggaac atagttaagt taatgagtgg aaaggatgtg ttttatcttc cacctgaaaa    7980
gtgtgacacc ctgttgtgtg acattggaga atcttcacca agcccaacag tggaagaaag    8040
cagaactata agagttttga agatggttga accatggctg aaaaacaacc agttttgcat    8100
taaagtattg aaccttaca tgccagccgt gattgagcac ctagaaagac tacaaggaa     8160 acacggagga atgcttgtga gaaatccact ttcacgaaac tccacgcacg aaatgtactg    8220
gatatctaat ggtacaggta acattgtctc ttcagtcaac atggtatcca gattgttact    8280
gaacaggttc acgatgacac acaggagacc taccatagag aaagatgtgg atttaggagc    8340
aggaactcga catgttaatg cggaaccaga acacccaac atggatgtca ttggggaaag     8400
aataaaaagg atcaaggagg agcataattc aacatggcac tatgatgacg aaaaccccta    8460
caaaacgtgg gcttaccacg gatcttatga agtcaaagcc acaggctcag cctcctccat    8520
gataaatgga gtcgtgaaac ttctcactaa accatgggat gtggtgccca tggtgacaca    8580
gatggcaatg acagatacaa ctccatttgg ccagcagaga gtctttaaag agaaagtgga    8640
caccaggaca cccaggccta tgccagggac aagaaaggtt atggagatca cagcggagtg    8700
gctctggaga acccctggaa ggaacaaaag acccaggtta tgcacaaggg aagagtttac    8760
aaaaaaggtc agaaccaacg cagccatggg cgccgttttc acagaggaga accaatggga    8820
cagtgcgaaa gctgctgttg aggatgaaga gttttggaaa cttgtggaca gagaacgtga    8880
actccacaaa ttgggcaagt gtggaagctg tgtttacaac atgatgggca agagagagaa    8940
gaaacttgga gagtttggca aagcaaaagg cagtagagct atatggtaca tgtggttggg    9000
atccaggtac cttgagttcg aagcccttgg attcttaaat gaagaccact ggttctcgcg    9060
tgaaaactct tacagtggag tagaaggaga aggactgcac aagctaggct acatattaag    9120
ggatatctcc aagatacccg gaggagccat gtatgctgat gacacagctg ttggacacc     9180 aagaataaca gaagatgacc tgcacaatga ggaaaagatc acacagcaaa tggacctga    9240 acacaggctt ttagcgaacg ctatattcaa gctcacatac caaaacaaag tggtcaagt     9300 tcaacgaccg actccaacgg gcacggtaat ggacatcata tctaggaaag accaaaggg     9360
```

```
cagtggacag gtgggaactt atggtctgaa tacatttacc aacatggaag cccagttagt    9420
cagacaaatg gaaggagaag gtgtgctgtc aaaggcagac ctcgagaacc ctcatctgcc    9480
agaaaagaaa attacacaat ggttggaaac caaaggagtg gagaggttaa aaagaatggc    9540
cattagcggg gatgattgcg tagtgaaacc aattgatgac aggttcgcta acgccctgct    9600
tgctctgaac gatatgggaa aggttcggaa agacatacct caatggcagc catcaaaggg    9660
atggcatgac tggcagcagg ttcctttctg ctcccaccac tttcatgaat tgatcatgaa    9720
agatggaaga aagttggtgg ttccctgcag accccaggac gaactaatag gaagagcaag    9780
aatctctcaa ggagcgggat ggagcctttag agaaaccgca tgtttgggga aagcctacgc    9840
ccaaatgtgg agtctcatgt attttcacag aagagatctc agactagcgt ccaatgccat    9900
atgttcagca gtaccagtcc actgggtccc cacaagtaga acgacatggt ctattcatgc    9960
tcaccatcag tggatgacca cagaagacat gcttactgtt tggaacaggg tgtggatcga   10020
ggacaatcca tggatggaag acaaaactcc agttacaacc tgggaaaatg ttccatacct   10080
agggaagaga gaagaccaat ggtgcggatc acttatcggt ctcacttcca gagcaacctg   10140
ggcccagaac atacccacag caattcaaca ggtgagaagc cttataggca atgaagagtt   10200
tctggactac atgccttcaa tgaagagatt caggaaggag gaggagtcgg agggagccat   10260
ttggtaaacg taggaagtga aaagaggct aactgtcagg ccaccttaag ccacagtacg   10320
gaagaagctg tgctgcctgt gagccccgtc aaggacgtt aaaagaagaa gtcaggcccc   10380
aaagccacgg tttgagcaaa ccgtgctgcc tgtagctccg tcgtggggac gtaaaacctg   10440
ggaggctgca aactgtggaa gctgtacgca cggtgtagca gactagcggt tagaggagac   10500
ccctcccatg acacaacgca gcagcggggc ccgagcactg agggaagctg tacctccttg   10560
caaaggacta gaggttagag gagaccccccc gcaaacaaaa acagcatatt gacgctggga   10620
gagaccagag atcctgctgt ctcctcagca tcattccagg cacagaacgc cagaaaatgg   10680
```

<210> SEQ ID NO 13
<211> LENGTH: 10574
<212> TYPE: DNA
<213> ORGANISM: Dengue virus 4

<400> SEQUENCE: 13

```
ggacagttcc aaatcggaag cttgcttaac acagttctaa cagtttgttt taaatagaga      60
gcagatctct ggaaaaatga accaacgaaa aaaggtggtc agaccacctt tcaatatgct     120
gaaacgcgag agaaaccgcg tatcaacccc tcaagggttg gtgaagagat ctcaaccgg     180 acttttctcc gggaaaggac ctttgcggat ggtgctagca ttcatcacgt ttttgcgggt    240
cctttccatc ccaccaacag cagggattct gaaaagatgg ggacagttga aaagaacaa     300 ggccgtcaaa atactgattg gattcaggaa ggagataggt cgcatgttaa acatcttgaa    360
taggagaaga aggtcaacaa tgacattgct gtgtttgatt cccaccgtaa tggcgtttca    420
cctgtcaaca agagatggcg aacccctcat gatagtggca aaacacgaaa gggggagacc    480
tctcttgttt aagacaacag aagggatcaa caatgtacc cttattgcta tggacctggg    540
tgaaatgtgc gaagacactg tcacgtataa gtgtcctcta ctggttaaca ccgaacctga    600
agacattgac tgctggtgca atctcacgtc cacctgggtc atgtacggga catgcaccca    660
gaacggagaa cggagacgag agaagcgctc agtagctta acaccacatt caggaatggg    720
attggaaaca agagctgaga catggatgtc atcggaaggg gcttggaaac atgctcagag    780
```

```
agtagaaagc tggatactca gaaacccagg attcgcgctc ttggcaggat ttatggctta      840
catgattggg caaacaggaa tccagcgaat tgttttcttt gtcctgatga tgctagtcgc      900
cccatcctac ggaatgcgat gcgtaggggt agggaacaga gacttcgtgg aaggagtctc      960
gggtggagca tgggtcgact tggtgctaga acatggagga tgcgtcacaa ccatggccca     1020
gggaaagcca accttggatt tgaattgac taagacaaca gccaaggaag tagctctgtt     1080
aagaacctat tgcattgaag cctcgatatc aaacataacc acggcaacaa gatgtccaac     1140
gcaaggagag ccttatctca agaggagca agaccaacag tacatttgcc ggagagacgt      1200
ggtagacaga ggatgggca atggctgtgg cttatttgga aaaggaggag ttgtgacatg      1260
tgcaaagttt ttatgctcgg ggaagataac aggcaatctg gtccaaattg aaaaccttga     1320
atacacagta gtagtaacag tccacaatgg agacacccat gcagtaggaa atgcacatc      1380 caaccatgga gtgacagcca caataactcc taggtcacca tcggttgaag ttaaattgcc     1440
ggactatgga gaactaacac tcgattgcga gcccaggtcc ggaattgatt ttaatgagat     1500
gatcctgatg aagatgaaaa agaaaacgtg gcttgtgcat aagcaatggt ttttagacct     1560
acctctacca tggacggcag gagcagatac atcagaagtt cattggaatc ataaagagag     1620
aatggtgaca ttcaaggttc ctcatgccaa gagacaggat gtgacagtgc taggatctca     1680
ggagggagct atgcattctg ccctcgccgg agccacagaa gtggattctg gtgatggaaa     1740
tcacatgttt gcaggacatc tcaagtgcaa agtccgcatg gagaaattga gaattaaagg     1800
aatgtcatac acgatgtgtt caggaaagtt ctcaattgac aaagagatgg cagaaacaca     1860
gcatggaacc acagtggtga aagtcaagta tgaaggcgct ggagctccgt gtaaagttcc     1920
catagagata agagatgtga acaaggaaaa agtggtcgga cgtatcatct catctacccc     1980
ttttgctgag aataccaaca cgtaaccaa catagaatta gaacccccctt ttggggacag     2040 ctacatagtg ataggtgttg gagagagtgc attaacactc cattggttca gaaaagggag     2100
ctccattggc aagatgtttg agtccacata cagaggtgca aaacgaatgg ccattctagg     2160
tgaaacagct tgggatttg gctctgttgg tggactgttc acatcattgg gaaaggccgt     2220
acaccaggtt tttggaagtg tgtatacaac tatgttggga ggggtctcat ggatggttag     2280
aatcctaatt gggttcttag tattgtggat tggcacaaat tcaagaaaca cttcaatggc     2340
aatgacgtgc atagctgttg gaggaatcac tctgtttctg ggtttcacag ttcaagcaga     2400
catgggttgt gtggtgtcat ggaatgggaa ggaattaaaa tgtggaagcg aattttgt      2460 ggttgacaac gtacacactt ggacagaaca gtacaaattt caaccagagt ccccagcaag     2520
actagcgtct gcaatattga atgcccacaa agatgggtc tgtggaatta gatcaaccac     2580
gaggctggaa aatgttatgt ggaagcaaat aaccaatgag ctaaactatg ttctctggga     2640
aggaggacat gacctcactg tagtggctgg ggatgtgaag ggggtgttga ccaaaggcaa     2700
gagagcactc acacctccag tgaatgatct gaaatattca tggaagacat ggggaaagc      2760 aaaaatcttt acccccagaag caagaaacag tacgttttta atagacggac cagacacctc     2820
cgaatgcccc aatgagcgaa gagcatggaa cttttttgag gtagaagact atggatttgg     2880
catgttcacg accaacatat ggatgaaatt ccgagaagga agttcagaag tgtgtgacca     2940
tagactaatg tcggcggcaa tcaaagatca gaaagctgtg catgctgaca tgggttattg     3000
gatagagagc tcaaaaaacc agaccctggca gatagagaaa gcatccctta ttgaagtgaa     3060
aacatgtctg tggcccaaaa cccacacgct gtggagcaat ggagtgctgg aaagtcagat     3120
gctcattcca agatcatatg caggccccctt ttcacagcac aattaccgtc agggctatgc     3180
```

```
cacgcaaacc gtgggcccat ggcacctagg caaattggag atagactttg gagaatgccc   3240
cgggacaaca gtcgcaattc gggaggattg tgaccacaga ggcccatctt tgagaaccac   3300
cactgcatct ggaaaactgg tcacgcaatg gtgctgccgc tcctgcacga tgcctccctt   3360
aaggttcttg ggagaagatg gatgttggta tgggatggag atcaggcctc tgagtgaaaa   3420
agaagagaac atggtcaaat cacaggtaac ggccggacag ggcacatcag aaacttttc    3480 tatgggctg ttatgcctga ccttgtttgt ggaagaatgc ttgaggagaa gagttactag    3540
gaaacacatg atattggttg tggtaatcac cttttgcgct atcatcctag gaggtctcac   3600
atggatggac ttactacgag cccttatcat gttaggggat actatgtctg gtagaatagg   3660
aggacagatc cacctagcca tcatggcagt gtttaagatg tcaccaggat acgtgctggg   3720
tgtgttttta aggaaactta cttcaagaga cacagcgctg atggtaatag gaatggccat   3780
gacaacggtg ttttcaatcc cacatgacct catggaactc attgatggaa tatcattggg   3840
gttgatatta ctaaaaatag taacacattt tgacaacact caagtgggaa ccctagccct   3900
ttccttgact tttttaagat caacaatacc attagtcatg cttggagga ccattatggc    3960 tgtgttcttt gtggtcacac tcattccttt gtgcaggaca agctgtcttc aaaaacattc   4020
ccactgggta gaaataacag cactcatcct aggagcccag gctttgccag tgtacctaat   4080
gactctcatg aagggagcct caaggagatc ttggcctctc aatgagggca taatggctgt   4140
aggtttggtg agcctcttag gaagcgccct cttgaagaat gatgttcctt ggctggccc    4200 aatggtggca ggaggcttgc ttctagcggc ttacgtaatg agtggtagct cagcagacct   4260
gttactagag aaagctgcca acgtgcagtg ggatgaaatg gcggacataa ctggctcaag   4320
cccaatcata gaagtgaagc aggatgaaga tggctctttt tccatacggg acgtcgagga   4380
aaccaatatg atgactctct tggtgaaact ggcactgata acagtatcag gtctttaccc   4440
cttggcaatt ccagtcacaa tggcattatg gtatatttgg caagtgaaga cacaaagatc   4500
aggagctctg tgggacgtcc cctcacccgc tgccacccag aaagccacac tgtctgaagg   4560
agtgtatagg attatgcaaa gagggctgtt tgggaaaact caagttggag taggaataca   4620
catggaaggc gtatttcaca caatgtggca tgtaacaagg ggatcagtga tctgccatga   4680
gacagggaga ttagagccat cttgggctga cgtcagaaac gacatgatat catacggtgg   4740
gggatggagg ctcggagaca atgggacaa agaagaagat gttcaggttt tagccataga    4800
accagggaaa aatcccaaac atgtccaaac gaaacctggc ctttcaaga ccctaactgg     4860 agaaattgga gcagtaactc tggatttcaa acccggaacg tctggctctc ccattattaa   4920
caagaaaggg aaagttattg gactctatgg aaatggagtg ttaccaaat caggtgatta    4980 tgtcagtgcc ataacgcaag ccgagagaat tggtgagcca gattatgaag tagatgagga   5040
catttttcga aagaaagatt aaccataat ggatttacac cctggagctg aaagacaaa     5100 aagaatcctc ccatcaatag tcagagaggc cttaaaaagg aggctgcgaa ccctgatttt   5160
agctcccacg agagtggtgg cggccgagat ggaagaggcc ctacgtggat tgccaatccg   5220
ttatcagact ccagctgtga atcagagca cacaggaaga gagattgtag acctcatgtg    5280
tcatgcaacc tttacaacaa gacttttgtc atcaaccagg gttcctaatt ataacctcat   5340
agtgatggat gaagcacatt tcactgaccc ttgcagtgtc gcggctagag ggtacatttc   5400
aaccagggtg gaaatgggag aggcagcagc tatcttcatg actgcaaccc ctcctggagc   5460
gacagatccc ttcccccaga gcaacagccc aatagaagac atcgagaggg aaattccaga   5520
```

-continued

```
aaggtcatgg aacacagggt tcgactggat aacagactac caagggaaaa ctgtgtggtt    5580
tgttcccagc ataaaagctg gaaatgacat tgcaaattgt ttgagaaagt cgggaaagag    5640
agtgatccag ttgagcagga aaacctttga cacggagtat ccaaagacga aactcacgga    5700
ctgggatttt gtggtcacca cagatatatc tgaaatgggg gccaatttca gagctgggag    5760
agtgatagac cccaggagat gcctcaagcc agttatccta acagatgggc cagagagagt    5820
tattctagca ggtccaatcc cagtaactcc agcaagtgcc gctcagagaa gagggcgaat    5880
aggtaggaat ccagcacagg aagatgacca atatgttttc tccggagacc cactaaaaaa    5940
tgatgaagat catgctcact ggacagaagc aaagatgctg cttgacaata tctacacccc    6000
tgaagggata attccaacac tgtttggtcc ggaaagggaa aaacccaag ccatcgatgg     6060
agagtttcgc ctcagagggg aacaaaggaa gacttttgtg gaattaatga agagaggaga    6120
ccttccggtg tggctgagct acaaggtagc ttctgccggt atctcctaca agatcgaga    6180
atggtgcttc acaggagaaa ggaataacca aatttttagaa gaaaacatgg aggttgaaat    6240
ttggactaaa gagggagaaa agaaaaagct aaggccaaaa tggttggatg cacgtgtgta    6300
cgctgatccc atggctttga aggatttcaa ggagtttgcc agtggaagaa agagcataac    6360
tctcgacatc ctaacagaga ttgccagttt gccaacttac ctttcctcta aggccaagct    6420
ggctcttgac aacatagtca tgctccacac aacagaaaaa ggagggaggg cctaccaaca    6480
cgccctgaac gaactcccag aatcactgga aacgctcatg cttgtagctc tactaggtgc    6540
tatgacagca ggcatcttcc tgttttttcat gcaggggaaa ggaataggaa aattgtcaat    6600
gggtctaata gccatagctg tggctagtgg cttgctctgg gtagcagaaa ttcagcccca    6660
gtggatagca gcttcaatca tactggagtt cttttcttatg gtgctgttga taccagaacc    6720
agaaaaacaa aggaccccac aagacaatca attgatctac gtcatattga ccattctcac    6780
catcatcggt cttatagcag ccaatgagat ggggctgatt gaaaaaacaa aaactgactt    6840
tgggttttac caggtaaaaa cagaaacaac tattcttgat gtggatttga ccagcctc     6900
agcatggaca ctttatgcgg tagccaccac cattctgact cccatgctga cacaccat     6960
agaaaacacg tctgccaacc tatctctagc agccattgcc aaccaagcag ctgttctaat    7020
gggacttgga aaaggatggc cgctccacag aatggacctc ggtgtgccgc tgttagcaat    7080
aggatgttat tctcaagtga acccaacaac cctgacagca tccttagtca tgcttttagt    7140
ccattatgcc ataataggtc caggattgca ggcaaaagcc acgagagagg cccagaaaag    7200
gacagctgct gggatcatga agaaccccac ggtggacggg ataacagtaa tagatctaga    7260
accaatatcc tatgacccaa aatttgaaaa gcaattaggg caagtcatgc tactagtcct    7320
gtgtgctgga caattacttt tgatgagaac aacatgggct ctctgcgaag tcttgacttt    7380
ggccacagga ccagccatga cttgtgggg gggcaaccca ggaaggtttt ggaacacgac    7440
catagctgta tccacagcca acatttttcag aggaagctat ttggcaggag ctggactagc    7500
ttttttcgctc ataaagaatg cacaaacccc taggagggga actgggacca caggagagac    7560
actgggagag aagtggaaga cacagttaaa ctcattagac agaaaagagt ttgaagagta    7620
caaaagaagt ggaatactag aagtggatag gactgaagcc agtctgcccc taaaagatgg    7680
atctaaaatc aagcatgcgg tgtccagagg gtctagtaag atcagatgga ttgttgaaag    7740
agggatggtt aagccgaaag ggaaggtcgt ggatcttggt tgcggagggg gaggatggtc    7800
ctattacatg gcgacactca agaacgtgac tgaagtgaaa ggatatacaa aaggaggtcc    7860
aggacatgag gaaccaatcc ccatggctac ttatggctgg aacttggtca aactccattc    7920
```

```
aggggttgat gtgttttaca aacccactga gcaggtggac accttgctct gtgacattgg   7980
ggagtcgtcc tctaatccga caatagagga aggaaggaca ttgagagtct tgaagatggt   8040
agagccatgg ctctcttcaa aacctgagtt ctgcatcaaa gtcctcaacc cctacatgcc   8100
aacagttata gaagagctgg agaaactcca gagaagatat ggcggaagcc tcgtcagatg   8160 cccttttatcc aggaattcca cccatgagat gtattgggtg tcaggtgcgt cgggaaacat   8220
cgtgagttct gtgaacacaa tatcaaagat gctgttgaac aggttcacaa caaggcatag   8280
gaaacccact tatgagaagg acgtggatct tggggcagga acgagaagtg tctccactga   8340
aacagaaaaa ccagacatga cagttattgg gagaaggctt cagagattgc aagaagagca   8400
caaagaaacc tggcactatg accaggaaaa cccatacaga acctgggcgt atcatggaag   8460
ctatgaagct ccttcgacag gctcagcatc ctccatggtg aacggggtag taaaactgct   8520
gacaaaaccc tgggatgtga ttccaatggt gacccagttg ccatgacag acacaacccc   8580 tttttgggcaa caaagagtgt tcaaggagaa ggtggatacc agaacaccac aaccaaaacc   8640
cggcacacga atgattatga ccacgacagc caattggctg tgggctctcc tcgggaagaa   8700
gaaaagtccc agattgtgta caagggaaga gttcatctca aaagttaggt caaatgcagc   8760
cataggcgca gtctttcagg aagaacaagg atggacatca gccagtgaag ctgtgaatga   8820
cagccggttc tgggaactgg ttgacaaaga aagggctctg caccaggaag gaaaatgtga   8880
atcgtgtgtc tataacatga tgggaaagcg tgagaaaaaa ttaggagagt tggtagggc   8940 caagggaagc cgagcaatct ggtacatgtg gctaggggcg cggttcctgg aatttgaagc   9000
cctgggtttc ttgaatgaag atcactggtt tagcagagaa aactcatgga gtggagtgga   9060
aggggaaggt ctgcacagat tgggatatat cttggaggat atagacaagc aggaaggaga   9120
tctaatatat gctgacgaca cagcaggctg ggacacgaga atcactgagg atgaccttttt   9180 aaatgaagaa ctgatcacag aacagatggc cccccatcac aagactctag ccaaagccat   9240
tttcaaacta acctatcaaa acaaagtggt gaaagtcctc agacccacac cgaaaggagc   9300
ggtgatggac atcatatcca ggaaagacca aagaggtagt ggacaggttg aacatatgg   9360 tttaaacaca ttcactaaca tggaagttca actcatccgc caaatggaag ctgaaggagt   9420
catcacacaa gacgacatgc agaacccaaa agggttgaaa gaaagagttg agaaatggct   9480
gacagagtgt ggcgtcgaca ggttgaagag gatggcaatc agtggagatg attgcgtggt   9540
gaagccccta gatgagaggt tcagcacctc cctcctcttc ttgaacgata tgggaaaggt   9600
gaggaaagac atccctcagt gggaaccatc caagggatgg aaaaactggc aagaggttcc   9660 ttttgctcc caccatttc ataagatctt tatgaaagat ggccgctcac tagttgttcc   9720
atgcagaaac caggatgaac tgataggaag agccagaatc tcgcaagggg ctggatggag   9780
cttaagagaa acagcctgtt tgggcaaagc ttacgcccaa atgtggtcgc ttatgtattt   9840
ccatagaagg gacctacgtt tagcctccat ggccatatgt tcagcagttc aacggaatg   9900 gtttccaaca agcaggacaa catggtcaat ccacgctcat caccagtgga tgaccactga  9960
agacatgctc aaagtgtgga acagggtgtg gatagaagac aaccccaata tgactgacaa  10020
gactccagtc cattcgtggg aagacatacc ttacctaggg aaaagagagg atttgtggtg  10080
tggatccctg attggactct cttccagagc cacctgggcg aagaacattc acggccat   10140 aacccaggtc aggaatctga tcggaaaaga ggactacgtg gattacatgc cagtcatgaa  10200
aagatacagc gctccttccg aaagtgaagg agttctgtaa ttactaataa caaacaccaa  10260
```

```
                                            -continued
agagaccatt gaagtcaggc cacttgtgcc acggcttgag caaaccgtgc tgcctgtagc    10320
tccgccaata atgggaggcg taaaattccc agggaggcca tgcgccacgg aagctgtacg    10380
cgtggcatat tggactagcg gttagaggag acccctccca tcactgacaa aacgcagcaa    10440 caaaggggc  ccgaagccag gaggaagctg tacttctggt ggaaggacta gaggttagag    10500 gagaccccc  caacacaaaa acagcatatt gacgctggga aagaccagag atcctgctgt    10560
ctctgcaaca tcaa                                                      10574
```

DENGUE VIRUS VACCINE

TECHNICAL FIELD

The present invention relates to a recombinant vaccinia virus as a dengue virus vaccine, and the like.

BACKGROUND ART

Dengue viruses are endemic primarily in the tropical areas, and about 400 million people are said to be annually infected with these viruses around the world, of which about 100 million people develop dengue fever. The dengue transmission area has been expanding (FIG. 1), and there was a report of mass infection (over 10,000 people infected) in China (Guangdong). In Japan, national incidence of infection in 2014 has settled, but Japan is exposed to a risk of a constant incidence of infection since the virus is transmitted every year via travelers and the like from the countries where infection is endemic. There have been over 200 imported cases reported since 2010.

At present, no clinically accessible therapeutic drug has been successfully developed, and only symptomatic treatments are available. Meanwhile, several dengue vaccines are reportedly undergoing clinical trials. Among them, the most successfully developed chimeric yellow fever-tetravalent dengue vaccine from Sanofi Pasteur has been approved in over 10 countries around the world including approval in Mexico in December, 2015 (FIG. 2). On 29 Nov. 2017, however, a report and a warning for use of the chimeric yellow fever-tetravalent dengue vaccine (CYD) from Sanofi Pasteur were issued from the manufacturer and WHO, saying that there is an increased risk of dengue fever or dengue hemorrhagic fever if the vaccine is used for vaccinating people who have never been infected with the virus (Non-patent document 1).

PRIOR ART DOCUMENT

Non-patent document 1: The World Health Organization (WHO), "WHO advises Dengvaxia be used only in people previously infected with dengue", 2017 (URL: https://www.who.int/medicines/news/2017/WHO-advises-dengvaxia-used-only-in-people-previously-infected/en/)

SUMMARY OF INVENTION

Under such circumstances, development of a dengue virus vaccine that can serve as a clinically accessible therapeutic or prophylactic drug, specifically, a dengue virus vaccine or the like that can suppress the risk of developing dengue fever and dengue hemorrhagic fever even when used for vaccinating people who have never been infected with the virus, has been desired.

The present invention was made in view of the above-described circumstances, and provides the following recombinant vaccinia virus, pharmaceutical composition and the like.

(1) A recombinant vaccinia virus comprising all or part of a cDNA encoding a non-structural protein from a dengue virus, and an expression promoter.

(2) The recombinant vaccinia virus according to (1) above, wherein the vaccinia virus is a DIs strain.

(3) The recombinant vaccinia virus according to either one of (1) and (2) above, wherein the cDNA encoding a non-structural protein is a cDNA encoding a NS1 region of a non-structural protein from a dengue virus.

(4) The recombinant vaccinia virus according to either one of (1) and (2) above, wherein the cDNA encoding a non-structural protein is a cDNA encoding a region other than the NS1 region of the non-structural protein from the dengue virus.

(5) The recombinant vaccinia virus according to (4) above, wherein the region other than the NS1 region of the non-structural protein is a region comprising NS2A, NS2B, NS3, NS4A, NS4B and NS5 regions.

(6) The recombinant vaccinia virus according to any one of (1)-(5) above, wherein the dengue virus is a dengue virus serotype 2.

(7) The recombinant vaccinia virus according to any one of (1)-(6) above, wherein the cDNA encoding a non-structural protein is DNA of (a)-(f) below:

(a) DNA comprising the nucleotide sequence represented by SEQ ID NO:1;

(b) DNA which has 80% or higher identity with DNA comprising a nucleotide sequence complementary to the nucleotide sequence represented by SEQ ID NO:1, and which codes for a non-structural protein from a dengue virus;

(c) DNA comprising the nucleotide sequence represented by SEQ ID NO:2;

(d) DNA which has 80% or higher identity with DNA comprising a nucleotide sequence complementary to the nucleotide sequence represented by SEQ ID NO:2, and which codes for a non-structural protein from a dengue virus;

(e) DNA comprising the nucleotide sequence represented by SEQ ID NO:3; and (f) DNA which has 80% or higher identity with DNA comprising a nucleotide sequence complementary to the nucleotide sequence represented by SEQ ID NO:3, and which codes for a non-structural protein from a dengue virus.

(8) A pharmaceutical composition comprising the recombinant vaccinia virus according to any one of (1)-(7) above.

(9) The pharmaceutical composition according to (8) above, which is a prophylactic drug for a dengue virus infectious disease.

(10) The pharmaceutical composition according to (8) above, which is a therapeutic drug for a dengue virus infectious disease.

EFFECT OF THE INVENTION

The present invention provides a recombinant vaccinia virus as a dengue virus vaccine which can serve as a clinically accessible therapeutic or prophylactic drug, a pharmaceutical composition using the same, and the like.

The recombinant vaccinia virus of the present invention is extremely advantageous in that, even when it is used as a dengue virus vaccine to vaccinate people who have never been infected with the virus, the subsequent risk of developing dengue fever or dengue hemorrhagic fever (in particular, highly severe dengue hemorrhagic fever) can be suppressed (for example, induction of pathology of a severe disease (dengue hemorrhagic fever, etc.) due to an antibody-dependent enhancement (ADE) phenomenon can be suppressed).

BREIF DESCRIPTION OF DRAWINGS

The patent or application file contains at least one drawing executed in color. Copies of this patent or patent application publication with color drawing will be provided by the USPTO upon request and payment of the necessary fee.

FIG. 1: A view showing current distribution of dengue virus infection around the world.

FIG. 2: A list of dengue vaccines under clinical development.

FIG. 3: A diagram showing a gene structure of a recombinant vaccinia virus containing dengue virus genes.

FIG. 4: A diagram showing the kinds of vaccines that can be developed according to the present invention.

FIG. 5: A diagram showing results from identifying expression of dengue virus NS1 protein.

Figure 6:
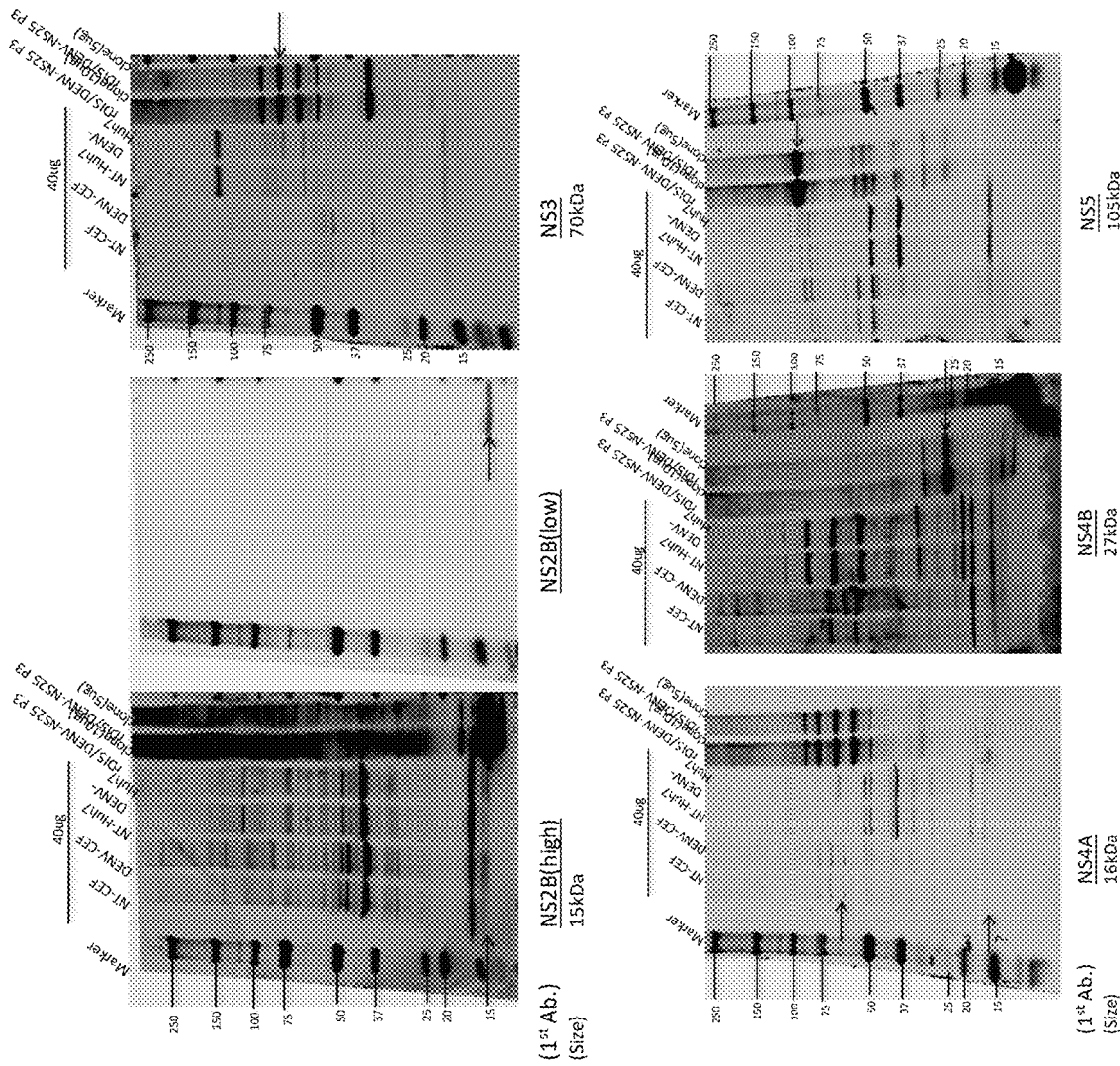

FIG. 6: A diagram showing results from identifying expressions of dengue virus NS2B, NS3, NS4A, NS4B and NS5 proteins.

Figure 7:
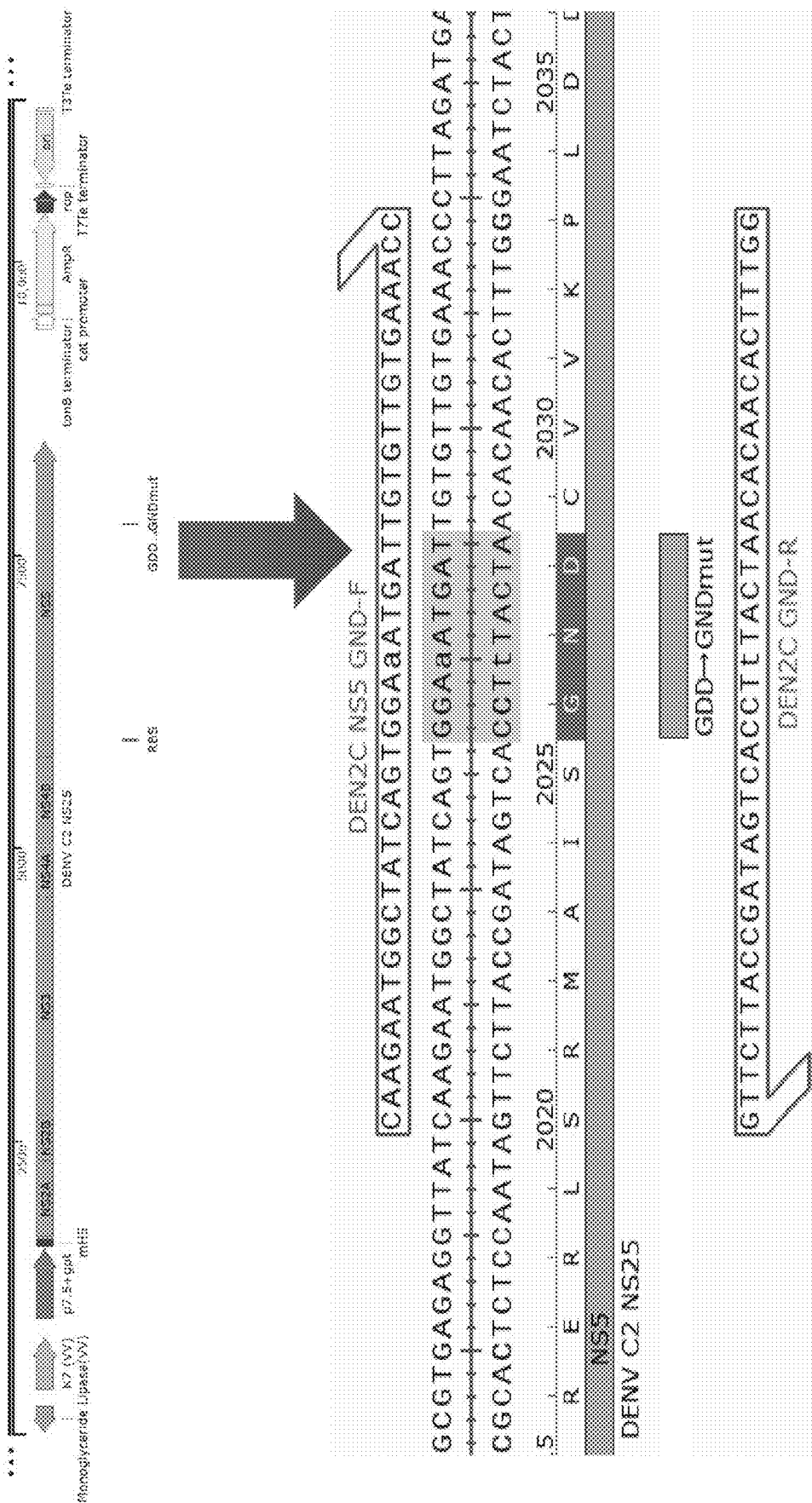

FIG. 7: A diagram showing that a mutant strain (rDIs-DENV2C-NS25-GND) that has amino acid substitution mutation in the NS5 region was prepared to further enhance the viral titer of rDIs-DENV2C-NS25.

Figure 8:

FIG. 8: A diagram showing that the viral growth rate rose by replacing with the mutant strain rDIs-DENV2C-NS25-GND.

FIG. 9: A diagram showing results of antibody induction by vaccination with the rDIs- DENV2C-NS1 vaccine.

Figure 10:
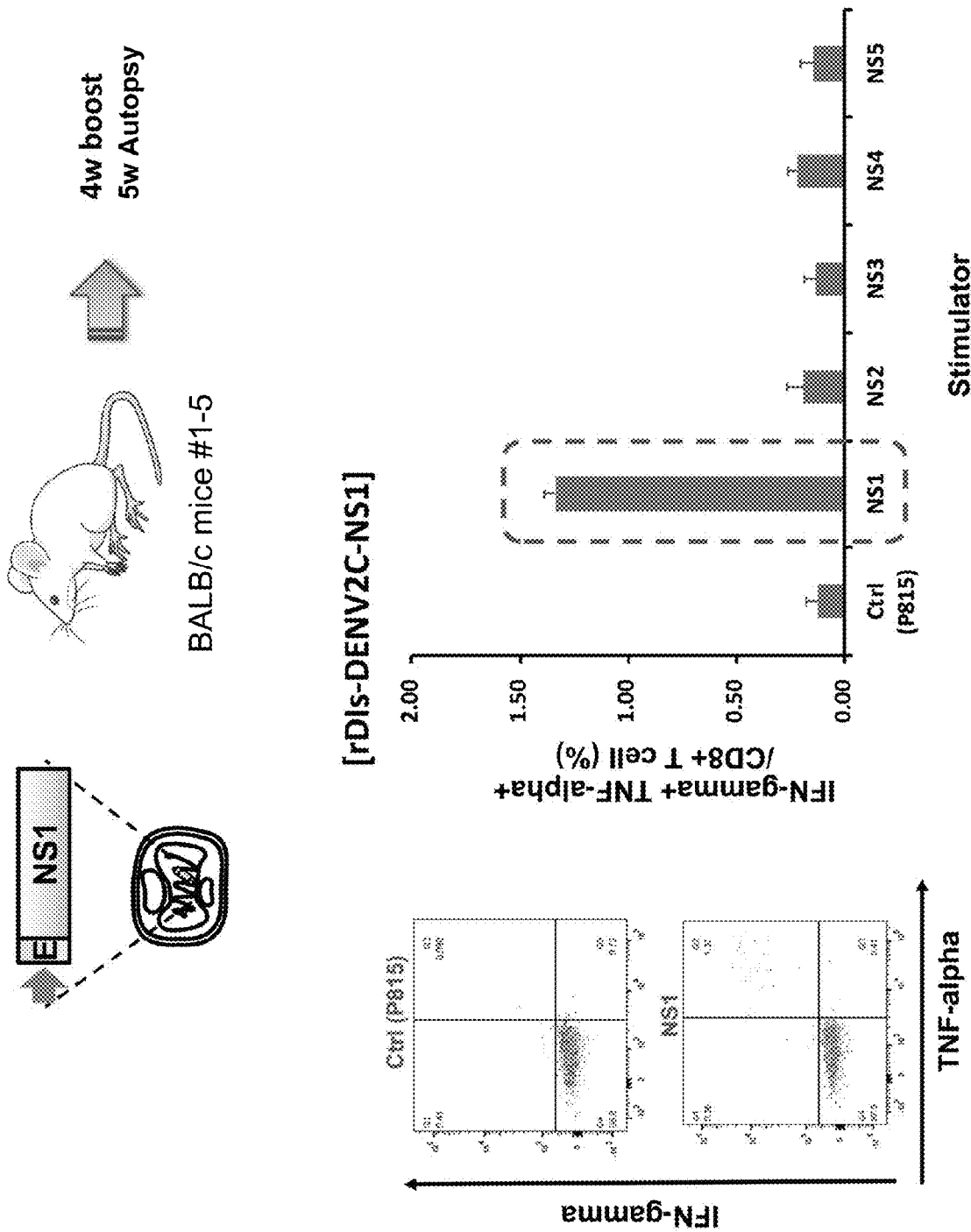

FIG. 10: A diagram showing results of induction of cellular immunity in rDIs- DENV2C-NS1-vaccinated mice.

Figure 11:
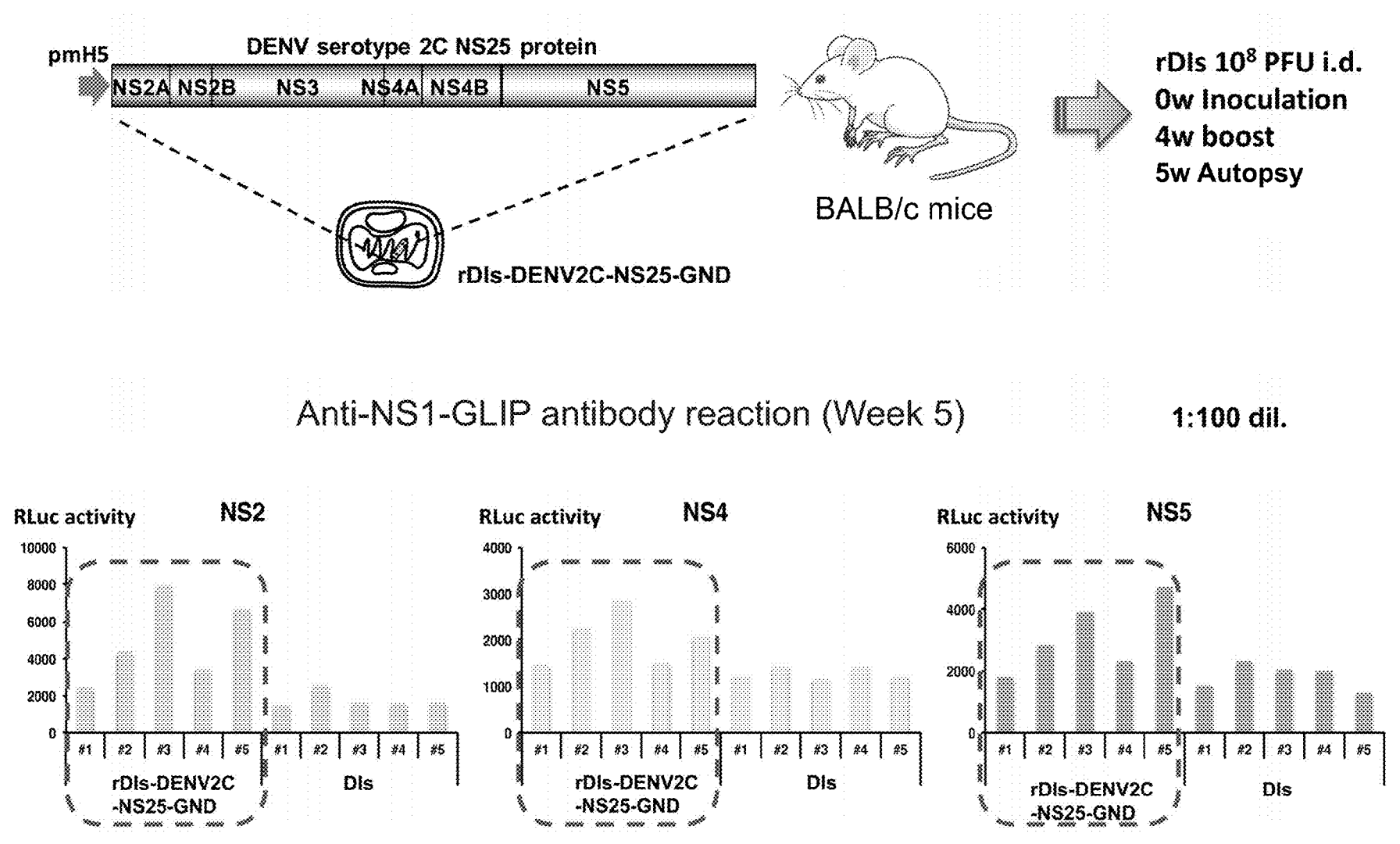

FIG. 11: A diagram showing antibody induction by vaccination with the rDIs- DENV2C-NS25-GND vaccine.

Figure 12:
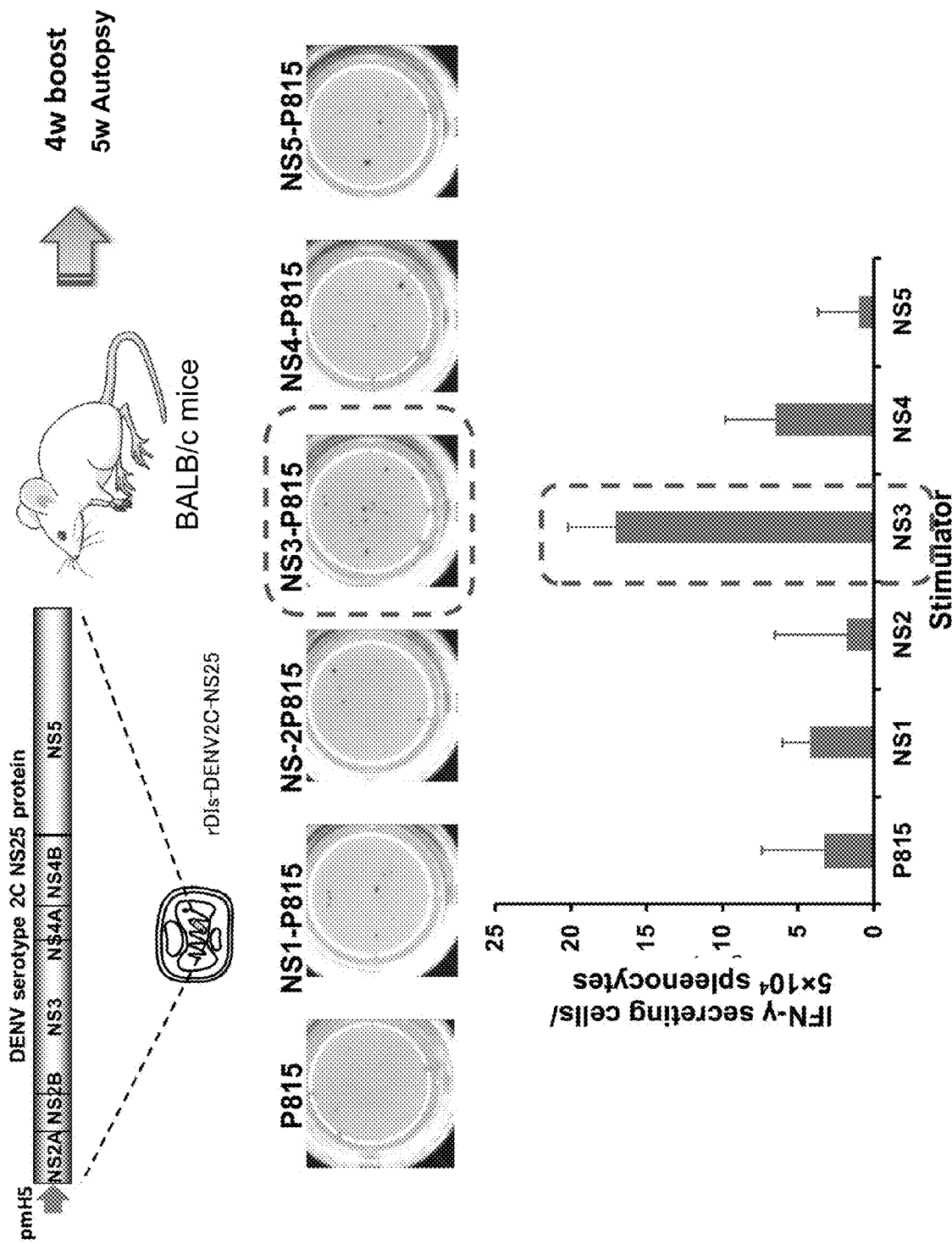

FIG. 12: A diagram showing results of induction of cellular immunity in rDIs- DENV2C-NS25-vaccinated mice.

Figure 13:
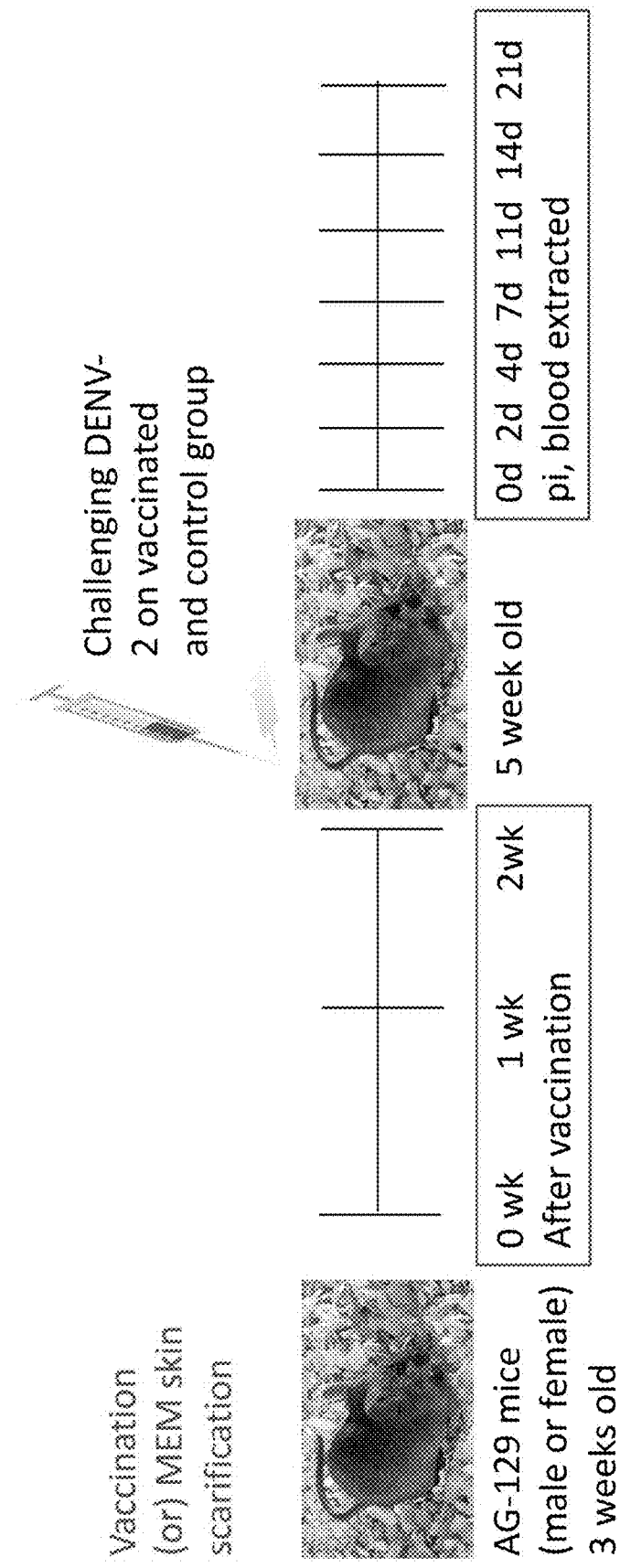

FIG. 13: A diagram showing a method for evaluating the protective effect of vaccination against infection, using AG129 mice.

Figure 14:
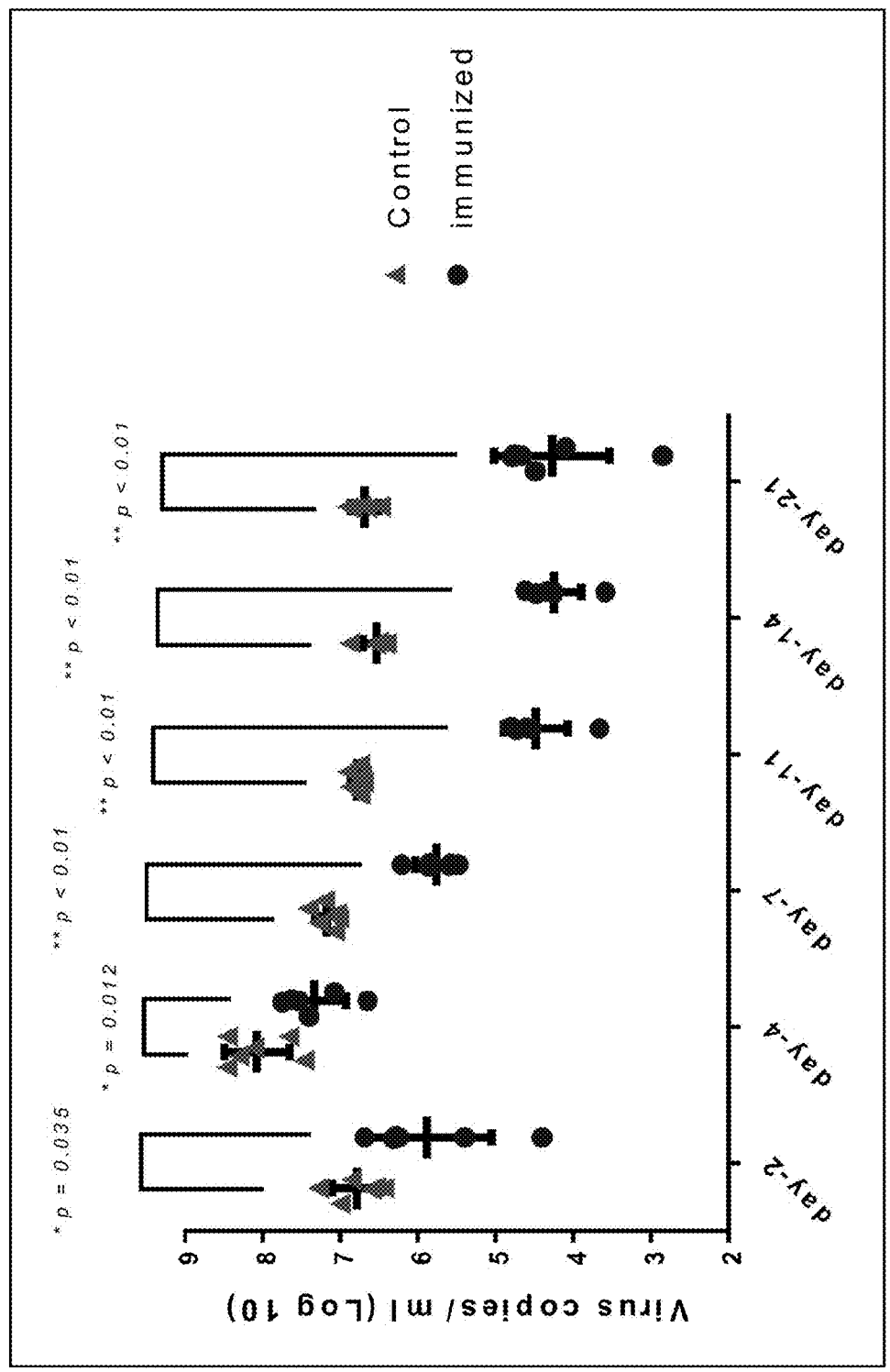

FIG. 14: A diagram showing results from evaluating the protective effect of vaccination against infection, using AG129 mice.

Figure 15:
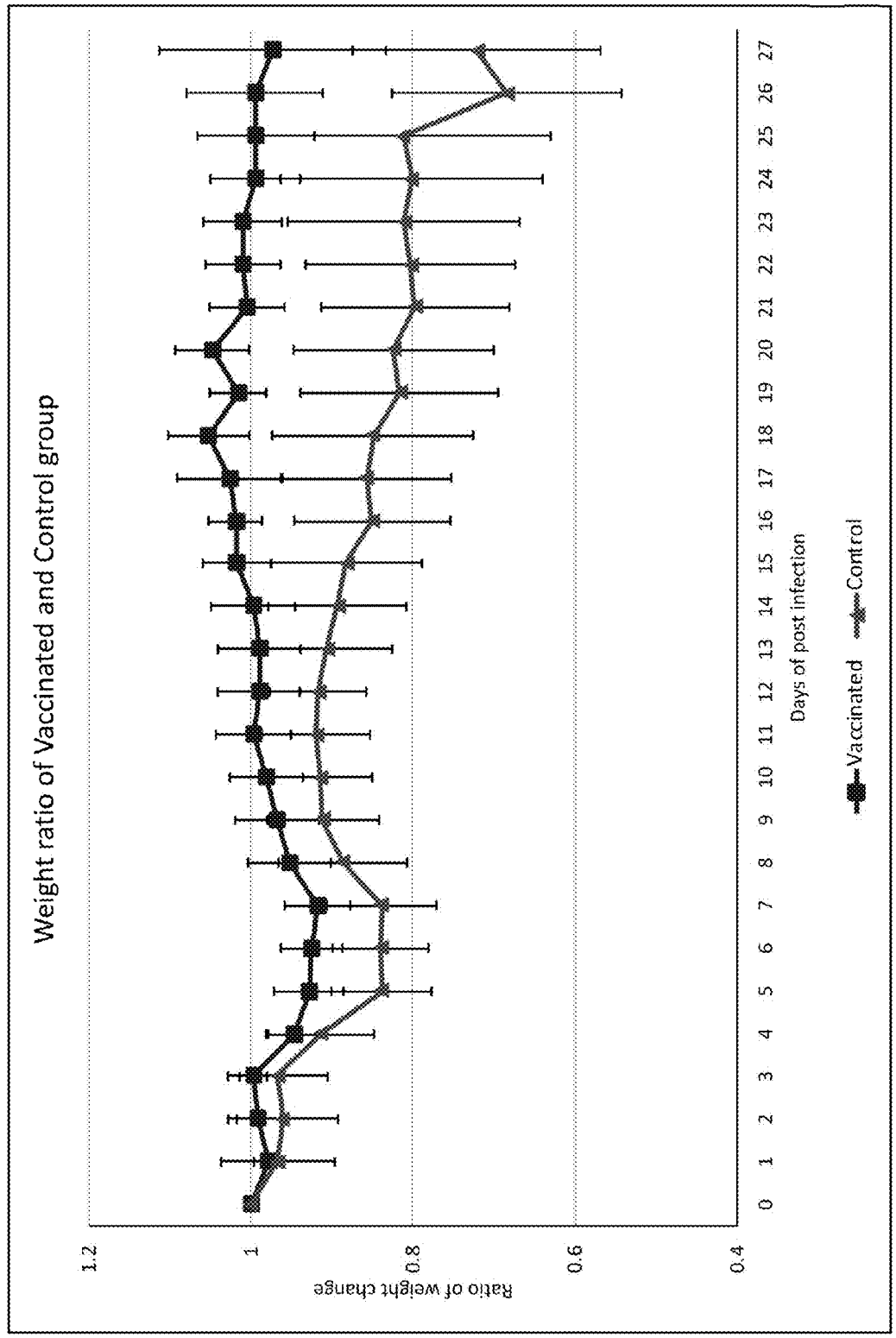

FIG. 15: A diagram showing results from evaluating the protective effect of vaccination against infection, using AG129 mice.

Figure 16:
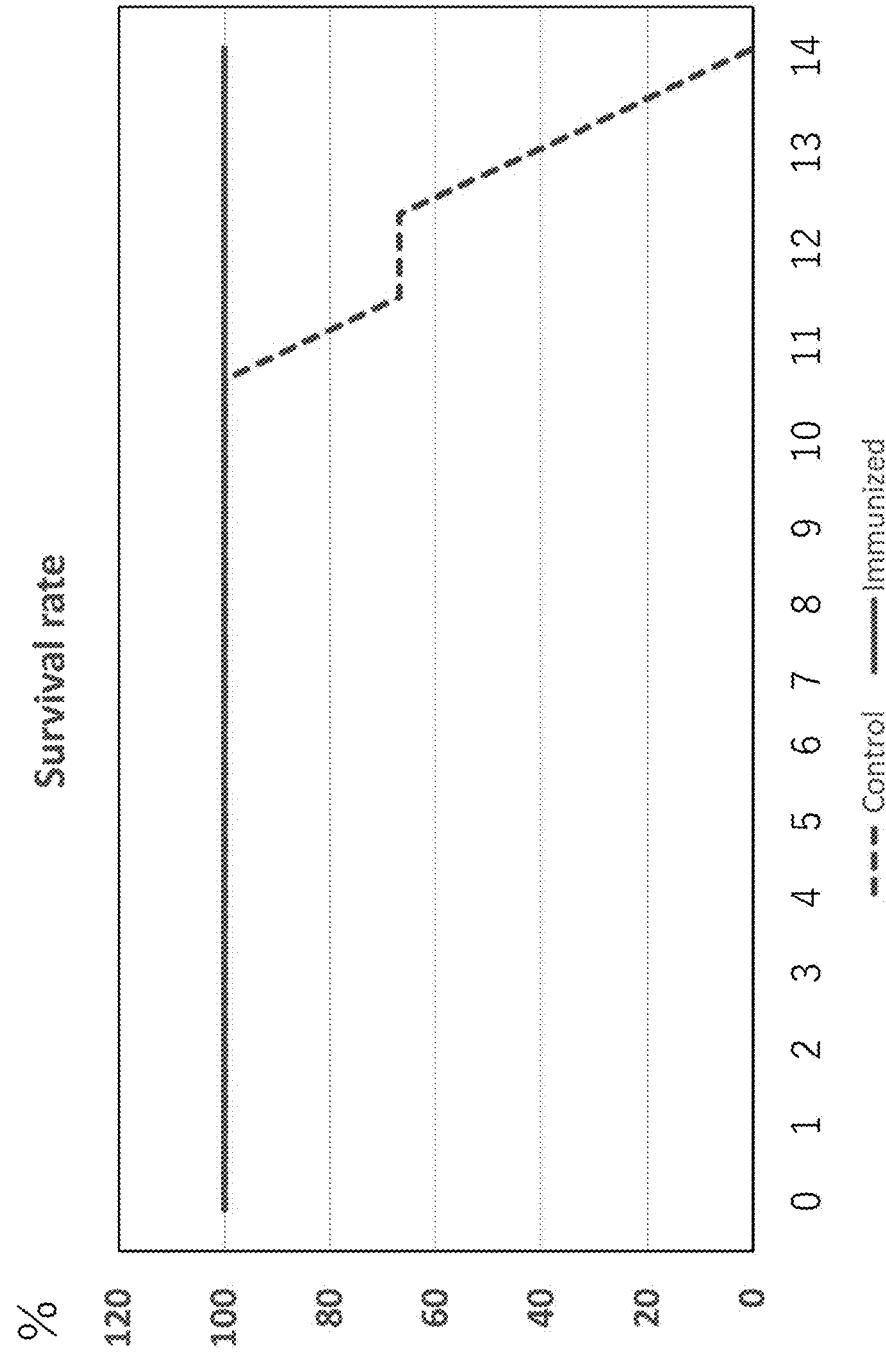

FIG. 16: A diagram showing results from evaluating the protective effect of vaccination against infection, using AG129 mice.

Figure 17:
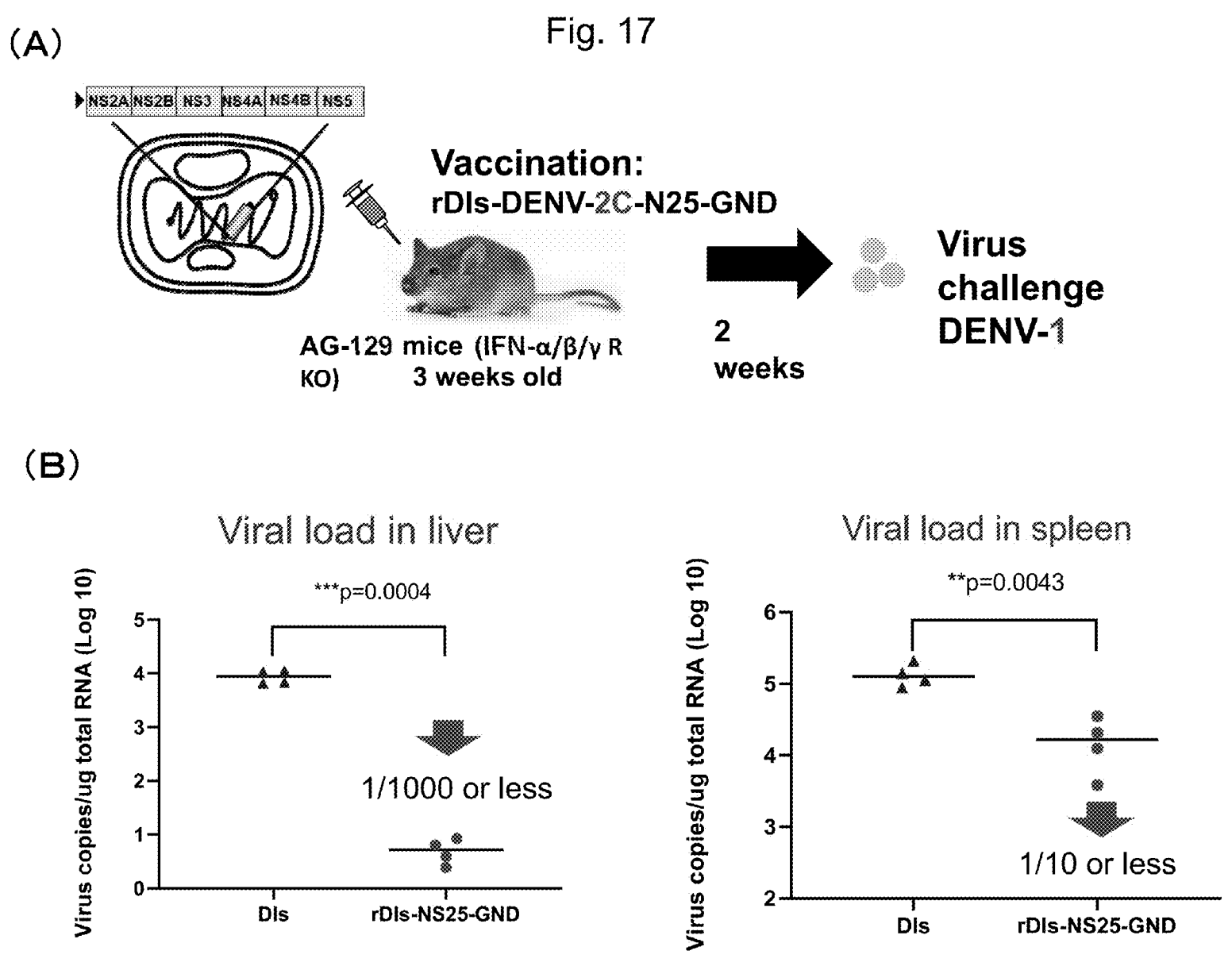

FIG. 17: (A) A diagram showing a method for evaluating the protective effect of vaccination against infection (specifically, the effect of eliminating a dengue virus of a serotype different from the serotype directly targeted by the vaccine (protective effect against infection)) using AG129 mice. (B) Charts showing the results from evaluating the protective effect of vaccination against infection (suppression of viral load in the liver and spleen) using said mice.

MODES FOR CARRYING OUT INVENTION

Hereinafter, the present invention will be described in detail. The scope of the present invention is not limited to these descriptions, and the present invention can be appropriately modified and carried out in a manner different from the example described below without departing from the spirit of the invention. The present specification incorporates all of the specification of Japanese Patent Application No. 2019-047582 (filed 14 Mar. 2019) based on which the present application claims priority. All of the publications including prior art documents, patent application publications, patent publications and other patent documents cited herein are incorporated herein by reference.

1. Brief Summary of the Invention

When a person who has been previously infected with a dengue virus (hereinafter, also referred to as DENV) is infected with a dengue virus belonging to a different serotype, excessive viral production is caused via a phenomenon called antibody-dependent enhancement (hereinafter, ADE) in which the antibody to the previous virus aids the secondary viral infection, leading to development of a severe disease such as dengue hemorrhagic fever. Therefore, a vaccine effective for viruses of the four serotypes, which does not induce these pathologies is needed.

Since an antibody to the structural protein may induce ADE, the genes of the NS1 region and the NS2-5 region (a region other than the NS1 region; specifically, a region comprising NS2A, NS2B, NS3, NS4A, NS4B and NS5 regions) of the non-structural protein which has no chance of inducing ADE were each inserted into a recombinant vector that is used for preparing a DIs recombinant vaccine. These recombinant vectors were used in an attempt to establish recombinant vaccinia viruses (rDIs-DENV2C-NS1 and rDIs-DENV2C-NS25). Induction of cellular immunity was observed in animals inoculated with the established vaccinia viruses. In addition, when the animals inoculated with these vaccinia viruses as vaccines were challenged with a dengue virus, decrease and suppression of the viral loads were observed in the sera or the organs (liver, spleen, etc.) (FIGS. 14 and 17), showing remarkable protective effects (inhibition) against infection with different dengue virus serotypes (for example, serotype 1, etc.) as well as infection with the homologous serotype, including inhibition of weight loss (FIG. 15) and increase in survival rate (FIG. 16).

Thus, the present invention was achieved.

2. Preparation of Dengue Virus (DENV) Recombinant Vaccinia Virus

All of the genes coding for the dengue virus (DENV) protein, the gene coding for the capsid (structural) protein region and the genes coding for the non-structural protein region involved in replication have previously been cloned and kept in the forms of plasmids. Therefore, genes contained in a recombinant vaccinia virus of the present invention, namely, genes comprising the DENV non-structural protein region can be obtained by a common genetic engineering technique. For example, nucleic acid synthesis using a DNA synthesizer, which is a generally employed genetic engineering technique, can be employed. Moreover, a PCR technique in which a genetic sequence that serves as a template is isolated or synthesized and then primers specific to each gene are designed to amplify the genetic sequence using a PCR device, or a gene amplification technique using a cloning vector can be employed. These techniques can be carried out by those skilled in the art according to "Molecular cloning 4th ed. Cold Spring Harbor Laboratory Press (2012)" or the like. The resulting PCR product can be purified by a known method. In a preferred aspect, DNAs coding for the respective gene regions of DENV can be prepared by performing PCR using the DENV gene inserted into the above-described plasmid as a template and using primers specific to a region of interest (non-structural protein region) of the DENV gene.

According to the present invention, a DNA of a gene coding for a non-structural protein region among all DENV gene regions is used for preparing the recombinant vaccinia virus. The non-structural protein region is a region consisting of NS1, NS2A, NS2B, NS3, NS4A, NS4B and NS5 regions. According to the present invention, the NS1 region and the region other than the NS1 region (namely, a region comprising NS2A, NS2B, NS3, NS4A, NS4B and NS5 regions, i.e., NS2-5 region) are separately used. There are four serotypes DENV-1, 2, 3 and 4 (serotype 1, serotype 2, serotype 3 and serotype 4). Among them, DENV-2 can further be grouped into Asian subtype and Cosmopolitan subtype, and therefore there are mainly a total of five types of DENVs. As is common to all types of DENVs, the non-structural protein region is a region comprising NS1, NS2A, NS2B, NS3, NS4A, NS4B and NS5 regions. A recombinant vaccinia virus of the present invention can be prepared using a cDNA of a non-structural protein region from any type of DENV without limitation, but preferably one derived from DENV-2, more preferably one derived from Cosmopolitan subtype of DENV-2.

According to the present invention, the nucleotide sequence of the DNA encoding the NS1 region of the non-structural protein region derived from Cosmopolitan subtype of DENV-2 is represented by SEQ ID NO:1, and the nucleotide sequence of the DNA encoding the NS2-5 region thereof is represented by SEQ ID NO:2. In addition, a mutant DNA of the nucleotide sequence of the DNA encoding the NS2-5 region (DNA encoding a region having mutation in the NS5 part of the NS2-5 region (specifically, mutation that abolishes enzymatic activity of NS5)) is represented by SEQ ID NO:3. Besides the DNAs composed of the nucleotide sequences represented by SEQ ID NOS:1, 2 and 3, the following DNAs can also be used in the present invention.

A DNA which has 80% or higher, 90% or higher, 95% or higher, 98% or higher or 99% or higher identity (homology) with a DNA consisting of a nucleotide sequence complementary to the nucleotide sequence represented by SEQ ID NO:1, and which encodes a non-structural protein from a dengue virus (mutant DNA of NS1 region).

A DNA which has 80% or higher, 90% or higher, 95% or higher, 98% or higher or 99% or higher identity (homology) with a DNA consisting of a nucleotide sequence complementary to the nucleotide sequence represented by SEQ ID NO:2, and which encodes a non-structural protein from a dengue virus (mutant DNA of NS2-5 region).

DNA which has 80% or higher, 90% or higher, 95% or higher, 98% or higher or 99% or higher identity (homology) with a DNA consisting of a nucleotide sequence complementary to the nucleotide sequence represented by SEQ ID NO:3, and which encodes a non-structural protein from a dengue virus (mutant DNA of a region having mutation in the NS5 part of the NS2-5 region).

A DNA which hybridizes to a DNA consisting of a nucleotide sequence complementary to the nucleotide sequence represented by SEQ ID NO:1 under stringent conditions, and which encodes a non-structural protein from a dengue virus (mutant DNA of NS1 region).

A DNA which hybridizes to a DNA consisting of a nucleotide sequence complementary to the nucleotide sequence represented by SEQ ID NO:2 under stringent conditions, and which encodes a non-structural protein from a dengue virus (mutant DNA of NS2-5 region).

A DNA which hybridizes to a DNA consisting of a nucleotide sequence complementary to the nucleotide sequence represented by SEQ ID NO:3 under stringent conditions, and which encodes a non-structural protein from a dengue virus (mutant DNA of a region having mutation in the NS5 part of the NS2-5 region (specifically, mutation that abolishes enzymatic activity of NS5)).

Herein, "encoding a non-structural protein from a dengue virus" means that the DNA encodes a protein that is produced in the cell upon viral proliferation. Furthermore, the above-described gene encoding the non-structural protein comprises the full-length sequence as well as partial sequences thereof.

The above-described mutant DNA can be obtained by chemical synthesis. Alternatively, it can be obtained from a cDNA library or a genome library by a known hybridization technique such as colony hybridization, plaque hybridization, Southern blotting or the like, using a DNA consisting of the nucleotide sequence represented by SEQ ID NO:1, 2 or 3, or a fragment thereof as a probe. Moreover, the stringent conditions in the above-mentioned hybridization may be, for example, conditions of 0.1×SSC-10×SSC, 0.1%-1.0% SDS and 20° C.-80° C., more specifically, conditions in which prehybridization at 37° C.-56° C. for 30 minutes or longer is followed by 1-3 times of rinsing in 0.1×SSC, 0.1% SDS at room temperature for 10-20 minutes. For detailed procedure of the hybridization technique, see "Molecular cloning 4th Ed. Cold Spring Harbor Laboratory Press (2012)" or the like.

The recombinant vaccinia virus of the present invention can be prepared, for example, but not exclusively, by inserting a DNA having a nucleotide sequence coding for a non-structural protein region of DENV (a region of interest, NS1 or NS2-5) into an expression vector (plasmid) of interest, and transfecting this plasmid vector into a vaccinia virus that serves as a host. Examples of this expression vector include, but not limited to, pSMART (registered trademark) vector and the like, and an expression promoter contained in the recombinant vaccinia virus of the present invention may be any expression promoter conventionally used for expression of a vaccinia virus gene (for example, mH5 promoter, etc.).

Transfection of the plasmid vector into the host can be conducted by employing any known technique. For example, the above-described plasmid vector can be transfected into an animal cell which has been infected with an attenuated vaccinia virus DIs strain so as to induce homologous recombination in the genome of vaccinia virus, thereby preparing a recombinant vaccinia virus expressing the region of interest of the DENV non-structural protein.

The above-mentioned attenuated vaccinia virus DIs strain is a highly attenuated strain lacking host range gene established by one-day egg passage from smallpox vaccine Dairen (Dalian) strain (DIE), which can replicate only in Chick Embryo Fibroblast (CEF) cells, developed by Dr. Isamu Tagaya, the National Institute of Health (currently known as the National Institute of Infectious Disease) (Tagaya et al. Nature 1961). Owing to extensive gene deletion, it cannot replicate in most mammal cells including mice, guinea pigs, rabbits and humans. As a result, safety is assured even when it is used to inoculate an immunocompromised/immunosuppressed patient.

The prepared recombinant vaccinia virus can be subjected to PCR using the viral genome as a template and primers specific to the gene of the DENV non-structural protein region to confirm introduction of the gene of the non-structural protein region of interest.

In addition, expression of the non-structural protein of interest can be confirmed by Western blotting using an animal cell infected with the prepared recombinant vaccinia virus as a sample. The antibody used in Western blotting may be, for example, a commercially available antibody that specifically recognizes the non-structural protein region of interest or an antibody obtained by purifying IgG using Protein G from an antiserum prepared by immunization with a DENV polypeptide.

3. Pharmaceutical Composition for Preventing or Treating Dengue Virus Infectious Disease The present invention provides a pharmaceutical composition comprising the above-described recombinant vaccinia virus, more specifically, a pharmaceutical composition as a prophylactic or therapeutic drug for a dengue virus infectious disease. Examples of the dengue virus infectious disease include dengue fever, dengue hemorrhagic fever and the like.

The pharmaceutical composition of the present invention can be introduced into an organism by any known method, for example, an injection such as an intramuscular, intraperitoneal, intradermal or subcutaneous injection, nasal, oral or lung inhalation, or oral administration. Furthermore, the recombinant vaccinia virus contained in the pharmaceutical composition of the present invention can also be used in combination with an existing antiviral drug (for example, interferon). The mode of such combinational use is not particularly limited, and the recombinant vaccinia virus of the present invention can be administered simultaneously with the existing antiviral drug, or they may be introduced into an organism by administering one of them and then the other after a certain period of time.

In addition, the pharmaceutical composition of the present invention may be mixed with a known pharmacologically acceptable carrier such as an excipient, a filler, a binder or a lubricant, a buffer, a tonicity-adjusting agent, a chelating agent, a colorant, a preservative, an aroma chemical, a flavoring agent, a sweetener or the like.

The pharmaceutical composition of the present invention can be administered orally or parenterally depending on whether it is in a form of an oral preparation such as a tablet, a capsule, a powdered agent, granules, pills, a liquid agent or a syrup agent, or in a form of a parenteral preparation such as an injection, a topical agent, a suppository or eye drops. Preferable examples include a local injection such as an intradermal, intramuscular or intraperitoneal injection.

While a dosage can suitably be selected according to the kind of the active element, the administration route, the administration subject, the age, weight, sex and symptom of the patient as well as other conditions, a daily dosage of the recombinant vaccinia virus is about 1,000-1,000,000,000 PFU (plaque forming units), preferably about 100,000-100,000,000 PFU for oral administration, and about 100-1,000,000,000 PFU (plaque forming units), preferably about 1,000-100,000,000 PFU for parenteral administration. The virus can be administered once or in multiple doses a day.

Since the recombinant vaccinia virus of the present invention can be used as a vaccine for preventing or treating a dengue virus infectious disease, the antibody titer or the cellular immune response as a vaccine against the virus is preferably measured in advance.

For example, the antibody titer against the recombinant vaccinia virus of the present invention or the parent strain DIs strain can be determined by inoculating mice, rabbits or the like with these virus strains, and then collecting the sera with time to determine the ELISA titer, the NanoLuc (registered trademark) titer or the like against DENV protein in the sera. By doing so, gene expression of the dengue virus and presence of immune response in the inoculated individual can be confirmed. In mouse sera inoculated with the recombinant vaccinia virus of the present invention, an increase in the antibody titer against DENV protein was confirmed after a week from the inoculation.

Moreover, cellular immune response can be determined by inoculating mice with the recombinant vaccinia virus of the present invention or the parent strain DIs strain, and then isolating the spleen cells from the immunized mice to see if CD4- and CD8-positive cells specific to the DENV non-structural protein have been induced/activated by a FACS or ELISPOT assay. According to the present invention, when the spleen cells from the BALB/c mice immunized with the recombinant vaccinia virus of the present invention were co-cultured with target cells expressing any of the non-structural proteins, CD4- and CD8-positive T cells, which were activated in an antigen-specific manner, were detected.

Thus, immunization with the recombinant vaccinia virus of the present invention was found to induce cellular immunity specific to the DENV non-structural proteins in the BALB/c mice.

Hence, the recombinant vaccinia virus prepared by the present inventors was confirmed to induce humoral immunity and cellular immunity against DENV.

Furthermore, a recombinant vaccinia virus (dengue virus vaccine) according to the present invention has or expected to have an eliminating effect (protective effect against infection owing to immune response) not only against the dengue virus serotype that is primarily and directly targeted by said vaccinia virus but also against dengue virus serotypes other than said serotype (specifically, preferably, against two, three or all (four) kinds of dengue virus serotypes among the four kinds of serotypes) (in other words, it has cross-reactivity). The recombinant vaccinia virus according to the present invention is useful as a vaccinia virus (vaccine) which can suppress induction of pathology of a severe disease (dengue hemorrhagic fever, etc.) due to an antibody-dependent enhancement (ADE) phenomenon which has been a particular concern in dengue virus infection.

EXAMPLES

Hereinafter, the present invention will be described in more detail by means of examples, although the present invention should not be limited to these examples.

Example 1

1. Method (1) Preparation and Evaluation of a Recombinant Vaccinia Vaccine Containing Non-Structural Protein Genes of Dengue Virus i) Selection of dengue virus strain used for genetic recombination There are four dengue virus serotypes, namely, DENV-1, 2, 3 and 4. Among them, DENV-2 can further be grouped into Asian subtype and Cosmopolitan subtype, and therefore there are mainly a total of five types of DENVs. From results of phylogenetic analysis of the five types of dengue viruses, the gene of the Cosmopolitan subtype strain of the DENV-2 serotype, located near the center of the phylogenetic tree (Dengue-2: Cosmopolitan: o1 Sa-054), was selected as the vaccine candidate. The genetic sequence information of the five types of dengue viruses used for the analysis are shown below.

Dengue-1: Genotype-I, M-72, Myanmar 2013 clinical isolate (NCBI GenBank Accession number: KR051912) (SEQ ID NO:10)

Dengue-2: Asian I, M-82, Myanmar 2013 clinical isolate (NCBI GenBank Accession number: KR051902) (SEQ ID NO:11)

Dengue-2: Cosmopolitan, o1 Sa-054 (genetic sequence information of non-structural NS1 region: SEQ ID NO:1; genetic sequence information of non-structural NS2-5 region: SEQ ID NO:2)

Dengue-3: Isolate DEL-72 (NCBI GenBank Accession number: GQ466079.1) (SEQ ID NO:12)

Dengue-4: Strain GZ/9809/2012 (NCBI GenBank Accession number: KC333651.1) (SEQ ID NO:13)

ii) The gene of the non-structural protein region of DENV-2 Cosmopolitan subtype strain was cloned, and PCR was performed for the genes of the NS-1 and NS2-5 regions using the following "NS-1 region primers" and "NS2-5 region primers." The PCR product was digested with enzymes Sbf-I and AsiSI and inserted into a recombinant plasmid for DIs strain gene, namely, a modified vector of transfer vector pUC/DIs (Koji Ishii et. al, Virology 2001, 302, 433-444). Subsequently, the resultant was inserted into a recombinant vector used for preparing a DIs recombinant vaccine (FIG. 3). A GND mutation was introduced into the NS2-5 region according to the QuikChange protocol (QuikChange; Stratagene) using the following "mutant NS2-5 region primers". The recombinant vector was used to proceed establishment of the recombinant virus (FIG. 4). After confirming that the genetic sequence had been inserted into the recombinant DIs, expression of the dengue virus protein was confirmed by Western blotting (FIG. 5, 6).

```
<NS-1 region primers>
SbfI-mH5p-NS1-2420-F:
                                        (SEQ ID NO: 4)
5'_GGGCGGCCCTGCAGGAAAAATTGAAAATAAATACAAAGGTTCTTGAG GGTTGTGTTAAATTGAAAGCGAGAAATAATCATAAATAGCCTTGGCGatg

AGCACCTCTCTGTCTGTGTCACTAG 3'

NS1-SgfI (AsiSI)-3430-R:
                                        (SEQ ID NO: 5)
5'_GGGCGGCGCGATCGCTCACTATTAGGCTGTGACCAAAGAGTTGAC

CAA_3'

<NS2-5 region primers>
SbfI-mH5p-NS2-3474-F:
                                        (SEQ ID NO: 6)
GGGCGGCCCTGCAGGAAAAATTGAAAATAAATACAAAGGTTCTTGAG

GGTTGTGTTAAATTGAAAGCGAGAAATAATCATAAATAGCCTTGGCG atgGGACATGGGCAGATTGACAAC

SgfI (AsiSI)-NS5-10224-R:
                                        (SEQ ID NO: 7)
GGGCGGCGCGATCGCTCACATTTACCACAGGACTCCTGCCTCTTCC

<Mutant NS2-5 region primers>
 DEN2C NS5 GND-F:
                                        (SEQ ID NO: 8)
5'_CAAGAATGGCTATCAGTGGAaATGATTGTGTTGTGAAACC_3'

DEN2C NS5 GND-R:
                                        (SEQ ID NO: 9)
5'_GGTTTCACAACACAATCATtTCCACTGATAGCCATTCTTG_3'
```

PCR using the above-described NS-1 region primers (SEQ ID NOS:4 and 5) was carried out using the following reaction solution composition under the following reaction conditions.

| <Composition of reaction solution> | |
|---|---|
| Template cDNA (DENV-2C cDNA): | 1.0 μL |
| 5 × Q5 DNA polymerase buffer: | 5 μL |
| 2.5 mM dNTP: | 2.5 μL |
| Q5 DNA polymerase (2.0 U/μl): | 0.5 μL |
| F primer (10 μM): | 1.25 μL |
| R primer (10 μM): | 1.25 μL |
| Sterilized water: | 13.5 μL |
| Total: | 25 μL |

Reaction Conditions

Total of 35 cycles of "denaturation/separation at 98° C. (10 sec)->annealing at 71° C. (15 sec)->synthesis/extension at 72° C. (40 sec)".

PCR using the above-described NS2-5 region primers (SEQ ID NOS:6 and 7) was carried out using the following reaction solution composition under the following reaction conditions

| <Composition of reaction solution> | |
|---|---|
| Template cDNA (DENV-2C cDNA): | 1.0 μL |
| 5 × Q5 DNA polymerase buffer: | 5 μL |
| 2.5 mM dNTP: | 2.5 μL |
| Q5 DNA polymerase (2.0 U/μl): | 0.5 μL |
| F primer (10 μM): | 1.25 μL |
| R primer (10 μM): | 1.25 μL |
| Sterilized water: | 13.5 μL |
| Total: | 25 μL |

Reaction Conditions

Total of 35 cycles of "denaturation/separation at 98° C. (10 sec)->annealing at 72° C. (15 sec)->synthesis/extension at 72° C. (40 sec)".

Furthermore, QuikChange protocol using the above-described mutant NS2-5 region primers (SEQ ID NOS:8 and 9) was carried out using the following kit and reaction solution composition under the following reaction conditions.

QuickChange Lightning Site-Directed Mutagenesis kit (Stratagene #210518)

| <Composition of reaction solution> | |
|---|---|
| Template DNA (DENV-2C NS25 plasmid): | 1.0 μL |
| 10 × reaction buffer: | 2.0 μL |
| 2.5 mM dNTP: | 0.4 μL |
| F primer (50 ng/ul): | 1.0 μL |
| R primer (50 ng/ul): | 1.0 μL |
| QuickSolution reagent: | 0.6 μL |
| QuickChange Lightning Enzyme: | 0.4 μL |
| Sterilized water: | 13.6 μL |
| Total: | 20 μL |

Reaction Conditions

Total of 18 cycles of "denaturation/separation at 95° C. (20 sec)->annealing at 60° C. (10 sec)->synthesis/extension at 68° C. (6 min)".

iii) The candidate clones for recombinant DIs vaccine containing dengue virus gene were mass-cultured in advance for inoculating animals to examine antibody production and induction of cellular immunity.

During the process, the titer of the NS2-5 region gene-DIs recombinant virus (rDIs-DENV2C-NS25) was found to be low and thus the virus had difficulty in mass proliferation. Therefore, a mutant strain (rDIs-DENV2C-NS25-GND) in which enzymatic activity of dengue virus NS5 was deleted was prepared (FIG. 7).

(2) Evaluation of a Recombinant Vaccinia Vaccine Containing Non-Structural Protein Genes of Dengue Virus in Animals BALB/c and C57BL/6 mice were inoculated with the prepared NS-1 region- or NS2-5 region gene-containing DIs recombinant vaccine to evaluate the immune responses.

i) With the NS-1 region gene-DIs recombinant vaccine (rDIs-DENV2C-NS1), high antibody production and induction of cellular immunity were observed in the BALB/c and C57BL/6 mice.

ii) With the NS2-5 region gene-DIs recombinant vaccine (rDIs-DENV2C-NS25), antibody production against the NS2 region and induction of cellular immunity against the NS3 region were observed. Vaccine dose, number of vaccine doses, schedule and the like are further examined in detail.

(3) Selection of Dengue Virus Infection Animal Models and Evaluation of Vaccine Effectiveness Wild-type mice are poorly infected with a dengue virus and none of their animal models has been found to develop hemorrhagic fever by dengue virus infection. An animal model for dengue virus infection is requisite to examine the vaccine effectiveness. Accordingly, marmosets, tree shrews and gene-modified mice were used to evaluate susceptibility to infection and development of pathology.

i) Gene-Modified Mice

Wild-type mice are known to be poorly infected with a dengue virus and do not develop dengue fever. Therefore, mice deficient in the receptor for an interferon having an antiviral activity were studied for the possibility of their use as an animal model for infection and development of a disease. Type-I and type-II interferon receptor-knockout mice (AG129 mice) challenged with a dengue virus were found to develop a disease and die. These AG129 mice were inoculated with a recombinant vaccinia vaccine containing non-structural protein genes of dengue virus, and further challenged with a dengue virus (serotype 2). The vaccinated group showed excellent protective effect against infection as compared to the non-vaccinated group.

ii) Marmosets

Marmosets were inoculated with dengue viruses (serotype 1, serotype 2) to observe the clinical course including blood viral load, incidence of antibody induction and the like for 14 days.

iii) Tree Shrews

Tree shrews were inoculated with dengue viruses (serotype 1, serotype 2) to observe the clinical course including blood viral load, incidence of antibody induction and the like for 14 days.

2. Results (1) A mutant strain in which enzymatic activity of dengue virus NS5 was deleted (rDIs-DENV2C-NS25-GND) was prepared. With the rDIs-DENV2C-NS25-GND recombinant virus, the yield increased 4 times or more (FIG. 8).

(2) BALB/c and C57BL/6 mice were inoculated with the prepared DIs recombinant vaccines containing NS-1 region or NS2-5 region gene (rDIs-DENV2C-NS1, rDIs-DENV2C-NS25) to evaluate the immune responses.

i) With the NS-1 region gene-DIs recombinant vaccine (rDIs-DENV2C-NS1), high antibody production and induction of cellular immunity were observed in the BALB/c and C57BL/6 mice (FIGS. 9 and 10).

ii) With the NS2-5 region gene-DIs recombinant vaccine (rDIs-DENV2C-NS25), antibody production against the NS2 region and induction of cellular immunity against the NS3 region were observed. Vaccine dose, number of vaccine doses, schedule and the like are further examined in detail (FIGS. 11 and 12).

(3) AG129 mice were inoculated with the NS2-5 region gene-DIs recombinant vaccine (rDIs-DENV2C-NS25-GND) and two weeks later challenged with a dengue virus (serotype 2) to evaluate a protective effect against infection owing to immune response (FIG. 13). When the vaccinated animals were challenged with a dengue virus in this manner, decrease in the serum viral load (FIG. 14) and also noticeable protective effects against infection including inhibition of weight loss and increase in the survival rate were observed (FIGS. 15 and 16).

(4) Marmosets were inoculated with dengue viruses (serotype 1, serotype 2) to observe the clinical course including blood viral load, incidence of antibody induction and the like for 14 days. The virus was detected in the blood for 14 days, and an antibody against the viral particles and an antibody against the NS-1 region were produced, showing susceptibility to infection. Moreover, when marmosets were inoculated with DENV-1, 2, 3 and 4 to observe the clinical course, an anti-dengue virus antibody was produced, showing susceptibility to infection. In addition, all of DENV-1, 2, 3 and 4 were found to be occult blood-positive, showing abnormal findings in the kidneys. These findings show that the protective effect of the vaccines against infection can be evaluated in marmosets.

(5) Tree shrews were inoculated with dengue viruses (serotype 1, serotype 2) to observe the clinical course including blood viral load, incidence of antibody induction and the like for 14 days. The virus was detected in the blood for 14 days, and an antibody against the viral particles and an antibody against the NS-1 region were produced, showing susceptibility to infection. Tree shrews were inoculated with DENV-1, 2, 3 and 4 to observe the clinical course. All of the individuals produced an antibody against the NS-1 region and thus were found to be susceptible to infection. These findings show that the protective effect of the vaccines against infection can be evaluated in tree shrews. Currently, the dengue virus-DIs recombinant vaccines are used for inoculation to continuously evaluate the protective effect of the vaccines against infection and diseases.

3. Discussion

When a primary infection with a dengue virus is followed by a secondary infection with a dengue virus belonging to a different serotype, a phenomenon called antibody-dependent enhancement (ADE), in which the antibody to the first virus aids the secondary viral infection, causes excessive viral production, leading to development of a severe disease such as dengue hemorrhagic fever. Since a vaccine against the dengue virus non-structural protein does not produce an antibody that binds to the viral particles, there is no risk of causing ADE and thus it may be an effective prophylactic vaccine. A NS-1 region gene-DIs recombinant vaccine and a NS2-5 region gene-DIs recombinant vaccine showed antibody production and induction of cellular immunity in mouse experiments. When the vaccinated mice were further challenged with a dengue virus, noticeable virus elimination and protective effect against infection were observed. Therefore, the NS-1 region gene-DIs recombinant vaccine (rDIs-DENV2C-NS1) and the NS2-5 region gene-DIs recombinant vaccine (rDIs-DENV2C-NS25) were shown to be novel effective vaccines that can avoid the risk of ADE induction.

Example 2

Type-I and type-II interferon receptor-knockout mice (AG129 mice) were inoculated in the skin with $1 \times 10^8$ PFU (single dose) of the mutant strain (rDIs-DENV2C-NS25-GND) of the NS2-5 region gene-DIs recombinant virus (rDIs-DENV2C-NS25) prepared in Example 1. Two weeks later, these mice were challenged with a dengue virus 1 strain (serotype 1; NIID-02-17 strain) (subcutaneous infection) to evaluate a protective effect against infection owing to immune response (FIG. 17A).

13-16 days after the above-described infection, the viral loads in the livers and spleens of these mice were measured by quantitative RT-PCR. As a result, the viral load significantly decreased in the rDIs-DENV2C-N25-GND vaccinated group (vaccinated group) (FIG. 17B).

Hence, inoculation with rDIs-DENV2C-N25-GND was demonstrated to be effective in rapidly eliminating even a dengue virus of a different serotype (serotype 1). Thus, the recombinant vaccinia virus (dengue virus vaccine) of the present invention has an eliminating effect (a protective effect against infection owing to immune response) even against a dengue virus of a different serotype (preferably, against dengue viruses of all (four) serotypes). Therefore, the present invention is useful as a recombinant vaccinia virus that does not induce pathology of a severe disease (dengue hemorrhagic fever, etc.) due to an antibody-dependent enhancement (ADE) phenomenon which has been a particular concern in dengue virus infection.

4. Relevant Information and References (1) Jin-Won Youn, Yu-Wen Hu, Nancy Tricoche, Wolfram Pfahler, Mohamed Tarek Shata, Marlene Dreux, François-Loic Cosset, Antonella Folgori, Dong-Hun Lee, Betsy Brotman, and Alfred M. Prince. Evidence for Protection against Chronic Hepatitis C Virus Infection in Chimpanzees by Immunization with Replicating Recombinant Vaccinia Virus. JOURNAL OF VIROLOGY, Nov. 2008,82 (21): 10896˜10905. doi: 10.1128/JVI.01179-08

(2) FRANÇOIS HABERSETZER, GÉRALDINE HONNET, CHRISTINE BAIN, MARIANNE MAYNARD-MUET, VINCENT LEROY, JEAN-PIERRE ZARSKI, CYRILLE FERAY, THOMAS F. BAUMERT, JEAN-PIERRE BRONOWICKI, MICHEL DOFFOËL, CHRISTIAN TRÉPO, DELPHINE AGATHON, MYEW-LING TOH, MARTINE BAUDIN, JEAN-YVES BONNEFOY, JEAN-MARC LIMACHER, and GENEVIÈVE INCHAUSPÉ. A Poxvirus Vaccine Is Safe, Induces T-Cell Responses, and Decreases Viral Load in Patients With Chronic Hepatitis C. GASTROENTEROLOGY 2011;141: 890˜899. doi: 10.1053/j.gastro.2011.06.009

(3). Satoshi Sekiguchi, Kiminori Kimura, Tomoko Chiyo, Takahiro Ohtsuki, Yoshimi Tobita, Yuko Tokunaga, Fumihiko Yasui, Kyoko Tsukiyama-Kohara, Takaji Wakita, Toshiyuki Tanaka, Masayuki Miyasaka, Kyosuke Mizuno, Yukiko Hayashi, Tsunekazu Hishima, Kouji Matsushima and Michinori Kohara. Immunization with a recombinant vaccinia virus that encodes nonstructural proteins of the hepatitis C virus suppresses viral protein levels in mouse liver. PLoS ONE 7(12):e51656 (2012).

(4) Takeshi Wada, Michinori Kohara and Yasuhiro Yasutomi. DNA vaccine expressing the non-structural proteins of hepatitis C virus diminishes the expression of HCV proteins in a mouse model. Vaccine 31(50):5968-74, doi: 10.1016/j.vaccine.2013.10.037 (2013).

(5) Takahiro Ohtsuki, Kiminori Kimura, Yuko Tokunaga, Kyoko Tsukiyama-Kohara, Chise Tateno, Yukiko Hayashi, Tsunekazu Hishima, and Michinori Kohara. M2 macrophages play critical roles in progression of inflammatory liver disease in hepatitis C virus transgenic mice. J. Virology 2015 Oct 14;90(1):300-7. doi: 10.1128/JVI.02293-15.

INDUSTRIAL APPLICABILITY

A recombinant vaccinia virus of the present invention, a pharmaceutical composition using the same, and the like are extremely advantageous in that, even when they are used as a dengue virus vaccine to vaccinate people who have never been infected with the virus, the subsequent risk of developing dengue fever or dengue hemorrhagic fever (in particular, highly severe dengue hemorrhagic fever) can be suppressed (for example, induction of pathology of a severe disease (dengue hemorrhagic fever, etc.) due to an antibody-dependent enhancement (ADE) phenomenon can be suppressed).

SEQUENCE LISTING

Free text:
SEQ ID NO:3: Modified DNA
SEQ ID NO:4: Synthetic DNA
SEQ ID NO:5: Synthetic DNA
SEQ ID NO:6: Synthetic DNA
SEQ ID NO:7: Synthetic DNA
SEQ ID NO:8: Synthetic DNA
SEQ ID NO:9: Synthetic DNA

The invention claimed is:

1. A recombinant vaccinia virus comprising a cDNA encoding a non-structural protein from a dengue virus, and an expression promoter,
wherein the cDNA encoding a non-structural protein is DNA of (a)-(e) below:
(a) DNA coding a region consisting of NS2A, NS2B, NS3, NS4A, NS4B and NS5 regions;
(b) DNA consisting of the nucleotide sequence represented by SEQ ID NO:2;
(c) DNA which has 99% or higher identity with DNA consisting of a nucleotide sequence complementary to the nucleotide sequence represented by SEQ ID NO:2, and which codes for a non-structural protein from a dengue virus;
(d) DNA consisting of the nucleotide sequence represented by SEQ ID NO:3; and
(e) DNA which has 95% or higher identity with DNA consisting of a nucleotide sequence complementary to the nucleotide sequence represented by SEQ ID NO:3, and which codes for a non-structural protein from a dengue virus.

2. The recombinant vaccinia virus according to claim 1, wherein the vaccinia virus is a DIs strain.

3. The recombinant vaccinia virus according to claim 1, wherein the dengue virus is a dengue virus serotype 2.

4. A pharmaceutical composition comprising the recombinant vaccinia virus according to claim 1.

5. The pharmaceutical composition according to claim 4, which is a prophylactic drug for a dengue virus infectious disease.

6. The pharmaceutical composition according to claim 4, which is a therapeutic drug for a dengue virus infectious disease.

7. The recombinant vaccinia virus according to claim 1, wherein the cDNA encoding a non-structural protein is DNA of (a).

8. The recombinant vaccinia virus according to claim 1, wherein the cDNA encoding a non-structural protein is DNA of (b).

9. The recombinant vaccinia virus according to claim 1, wherein the cDNA encoding a non-structural protein is DNA of (c).

10. The recombinant vaccinia virus according to claim 1, wherein the cDNA encoding a non-structural protein is DNA of (d).

11. The recombinant vaccinia virus according to claim 1, wherein the cDNA encoding a non-structural protein is DNA of (e).

* * * * *